(12) United States Patent
Karabinis

(10) Patent No.: US 7,218,931 B2
(45) Date of Patent: May 15, 2007

(54) SATELLITE RADIOTELEPHONE SYSTEMS PROVIDING STAGGERED SECTORIZATION FOR TERRESTRIAL REUSE OF SATELLITE FREQUENCIES AND RELATED METHODS AND RADIOTELEPHONE SYSTEMS

(75) Inventor: Peter D. Karabinis, Cary, NC (US)

(73) Assignee: ATC Technologies, LLC, Reston, VA (US)

( * ) Notice: Subject to any disclaimer, the term of this patent is extended or adjusted under 35 U.S.C. 154(b) by 512 days.

(21) Appl. No.: 10/353,308

(22) Filed: Jan. 29, 2003

(65) Prior Publication Data
US 2003/0153308 A1 Aug. 14, 2003

Related U.S. Application Data

(63) Continuation-in-part of application No. 10/074,097, filed on Feb. 12, 2002, now Pat. No. 6,684,057, said application No. 10/353,308 is a continuation-in-part of application No. 10/180,281, filed on Jun. 26, 2002, now Pat. No. 6,999,720.

(60) Provisional application No. 60/393,287, filed on Jul. 2, 2002, provisional application No. 60/347,173, filed on Jan. 9, 2002, provisional application No. 60/322,240, filed on Sep. 14, 2001.

(51) Int. Cl.
*H04Q 7/20* (2006.01)
*H04B 7/185* (2006.01)

(52) U.S. Cl. .................. 455/427; 455/13.4; 455/447

(58) Field of Classification Search ................. 455/447, 455/446, 427, 430, 431, 422.1, 12.1, 13.4
See application file for complete search history.

(56) References Cited

U.S. PATENT DOCUMENTS 4,901,307 A 2/1990 Gilhousen et al.

(Continued)

FOREIGN PATENT DOCUMENTS

EP 0 506 255 A2 9/1992

(Continued)

OTHER PUBLICATIONS

Examination Report for European Application 03 733 886.0 on Apr. 13, 2005.

(Continued)

*Primary Examiner*—Tilahun Gesesse
(74) *Attorney, Agent, or Firm*—Myers Bigel Sibley & Sajovec

(57) ABSTRACT

A satellite radiotelephone system can include a space-based component and a plurality of ancillary terrestrial components. The space-based component is configured to provide wireless radiotelephone communications over a satellite radiotelephone frequency band. The plurality of ancillary terrestrial components are configured to terrestrially reuse at least one of the satellite radiotelephone frequencies, at least some of the ancillary terrestrial components terrestrially reusing the at least one of the satellite radiotelephone frequencies in a staggered sectorization. Related methods are also discussed.

48 Claims, 12 Drawing Sheets

U.S. PATENT DOCUMENTS

| | | | |
|---|---|---|---|
| 5,073,900 A | 12/1991 | Mallinckrodt | |
| 5,303,286 A | 4/1994 | Wiedeman | |
| 5,327,572 A | 7/1994 | Freeburg | 455/13.1 |
| 5,339,330 A | 8/1994 | Mallinckrodt | |
| 5,365,571 A * | 11/1994 | Rha et al. | 455/446 |
| 5,394,461 A | 2/1995 | Freeburg | |
| 5,394,561 A * | 2/1995 | Freeburg | 455/428 |
| 5,432,780 A | 7/1995 | Smith et al. | |
| 5,446,756 A | 8/1995 | Mallinckrodt | |
| 5,448,623 A | 9/1995 | Wiedeman et al. | |
| 5,485,631 A | 1/1996 | Bruckert | |
| 5,511,233 A | 4/1996 | Otten | |
| 5,555,257 A | 9/1996 | Dent | |
| 5,584,046 A * | 12/1996 | Martinez et al. | 455/13.1 |
| 5,612,703 A | 3/1997 | Mallinckrodt | |
| 5,619,525 A | 4/1997 | Wiedeman et al. | |
| 5,631,898 A | 5/1997 | Dent | |
| 5,734,983 A * | 3/1998 | Faruque | 455/450 |
| 5,761,605 A | 6/1998 | Tawil et al. | |
| 5,765,098 A | 6/1998 | Bella | |
| 5,812,947 A | 9/1998 | Dent | |
| 5,832,379 A | 11/1998 | Mallinckrodt | |
| 5,835,857 A | 11/1998 | Otten | |
| 5,848,060 A | 12/1998 | Dent | |
| 5,850,608 A * | 12/1998 | Faruque | 455/447 |
| 5,852,721 A | 12/1998 | Dillon et al. | |
| 5,878,329 A | 3/1999 | Mallinckrodt | |
| 5,884,142 A | 3/1999 | Wiedeman et al. | |
| 5,907,541 A | 5/1999 | Fairholm et al. | |
| 5,926,758 A | 7/1999 | Grybos et al. | |
| 5,937,332 A * | 8/1999 | Karabinis | 455/12.1 |
| 5,940,753 A | 8/1999 | Mallinckrodt | |
| 5,960,349 A | 9/1999 | Chheda et al. | |
| 5,991,345 A | 11/1999 | Ramasastry | |
| 5,995,832 A | 11/1999 | Mallinckrodt | |
| 6,011,951 A | 1/2000 | King et al. | |
| 6,023,605 A | 2/2000 | Sasaki et al. | |
| 6,052,560 A | 4/2000 | Karabinis | |
| 6,052,586 A | 4/2000 | Karabinis | |
| 6,067,442 A | 5/2000 | Wiedeman et al. | |
| 6,072,430 A | 6/2000 | Wyrwas et al. | |
| 6,085,094 A | 7/2000 | Vasudevan et al. | |
| 6,091,933 A | 7/2000 | Sherman et al. | |
| 6,091,936 A * | 7/2000 | Chennakeshu et al. | 455/63.3 |
| 6,097,752 A | 8/2000 | Wiedeman et al. | |
| 6,101,385 A | 8/2000 | Monte et al. | |
| 6,108,561 A | 8/2000 | Mallinckrodt | |
| 6,134,437 A | 10/2000 | Karabinis et al. | |
| 6,157,811 A | 12/2000 | Dent | |
| 6,157,834 A | 12/2000 | Helm et al. | |
| 6,160,994 A | 12/2000 | Wiedeman | |
| 6,169,878 B1 | 1/2001 | Tawil et al. | |
| 6,198,730 B1 | 3/2001 | Hogberg et al. | |
| 6,198,921 B1 | 3/2001 | Youssefzadeh et al. | |
| 6,201,967 B1 | 3/2001 | Goerke | |
| 6,233,463 B1 | 5/2001 | Wiedeman et al. | |
| 6,240,124 B1 | 5/2001 | Wiedeman et al. | |
| 6,243,587 B1 * | 6/2001 | Dent et al. | 455/456.2 |
| 6,253,080 B1 | 6/2001 | Wiedeman et al. | |
| 6,256,497 B1 | 7/2001 | Chambers | |
| 6,289,221 B1 * | 9/2001 | Ritter | 455/447 |
| 6,311,074 B1 | 10/2001 | Luders | |
| 6,317,412 B1 * | 11/2001 | Natali et al. | 370/208 |
| 6,324,405 B1 | 11/2001 | Young et al. | |
| 6,339,707 B1 | 1/2002 | Wainfan et al. | |
| 6,339,708 B1 * | 1/2002 | Wang | 455/447 |
| 6,405,044 B1 * | 6/2002 | Smith et al. | 455/447 |
| 6,418,147 B1 | 7/2002 | Wiedeman | |
| 6,449,461 B1 | 9/2002 | Otten | |
| 6,522,865 B1 | 2/2003 | Otten | |
| 6,560,459 B1 * | 5/2003 | Wong | 455/447 |
| 6,628,919 B1 * | 9/2003 | Curello et al. | 455/12.1 |
| 6,684,057 B2 | 1/2004 | Karabinis | |
| 6,735,437 B2 * | 5/2004 | Mayfield et al. | 455/427 |
| 6,775,251 B1 | 8/2004 | Wiedeman et al. | |
| 6,785,543 B2 | 8/2004 | Karabinis | |
| 6,856,787 B2 | 2/2005 | Karabinis | |
| 6,859,652 B2 | 2/2005 | Karabinis et al. | |
| 6,879,829 B2 * | 4/2005 | Dutta et al. | 455/436 |
| 6,892,068 B2 * | 5/2005 | Karabinis et al. | 455/429 |
| 6,937,857 B2 | 8/2005 | Karabinis | |
| 6,975,837 B1 | 12/2005 | Santoru | |
| 6,999,720 B2 | 2/2006 | Karabinis | |
| 7,006,789 B2 | 2/2006 | Karabinis et al. | |
| 2001/0046866 A1 | 11/2001 | Wang | |
| 2002/0041575 A1 | 4/2002 | Karabinis et al. | |
| 2002/0122408 A1 | 9/2002 | Mullins | |
| 2002/0146979 A1 | 10/2002 | Regulinski et al. | |
| 2002/0177465 A1 | 11/2002 | Robinett | |
| 2003/0003815 A1 | 1/2003 | Yamada | |
| 2003/0022625 A1 | 1/2003 | Otten et al. | |
| 2003/0054761 A1 | 3/2003 | Karabinis | |
| 2003/0054762 A1 | 3/2003 | Karabinis | |
| 2003/0054814 A1 | 3/2003 | Karabinis et al. | |
| 2003/0054815 A1 | 3/2003 | Karabinis | |
| 2003/0068978 A1 | 4/2003 | Karabinis et al. | |
| 2003/0073436 A1 | 4/2003 | Karabinis et al. | |
| 2003/0149986 A1 | 8/2003 | Mayfield et al. | |
| 2003/0153308 A1 | 8/2003 | Karabinis | |
| 2003/0224785 A1 | 12/2003 | Karabinis | |
| 2004/0072539 A1 | 4/2004 | Monte et al. | |
| 2004/0102156 A1 | 5/2004 | Loner | |
| 2004/0121727 A1 | 6/2004 | Karabinis | |
| 2004/0142660 A1 | 7/2004 | Churan | |
| 2004/0192200 A1 | 9/2004 | Karabinis | |
| 2004/0192293 A1 | 9/2004 | Karabinis | |
| 2004/0192395 A1 | 9/2004 | Karabinis | |
| 2004/0203393 A1 | 10/2004 | Chen | |
| 2004/0203742 A1 | 10/2004 | Karabinis | |
| 2004/0240525 A1 | 12/2004 | Karabinis et al. | |
| 2005/0026606 A1 | 2/2005 | Karabinis | |
| 2005/0037749 A1 | 2/2005 | Karabinis et al. | |
| 2005/0041619 A1 | 2/2005 | Karabinis et al. | |
| 2005/0064813 A1 | 3/2005 | Karabinis | |
| 2005/0079816 A1 | 4/2005 | Singh et al. | |
| 2005/0090256 A1 | 4/2005 | Dutta | |
| 2005/0118948 A1 | 6/2005 | Karabinis et al. | |
| 2005/0136836 A1 | 6/2005 | Karabinis et al. | |
| 2005/0164700 A1 | 7/2005 | Karabinis | |
| 2005/0164701 A1 | 7/2005 | Karabinis et al. | |
| 2005/0170834 A1 | 8/2005 | Dutta et al. | |
| 2005/0181786 A1 | 8/2005 | Karabinis et al. | |
| 2005/0201449 A1 | 9/2005 | Churan | |
| 2005/0208890 A1 | 9/2005 | Karabinis | |
| 2005/0221757 A1 | 10/2005 | Karabinis | |
| 2005/0227618 A1 | 10/2005 | Karabinis et al. | |
| 2005/0239399 A1 | 10/2005 | Karabinis | |
| 2005/0239403 A1 | 10/2005 | Karabinis et al. | |
| 2005/0239404 A1 | 10/2005 | Karabinis | |
| 2005/0239457 A1 | 10/2005 | Levin et al. | |
| 2005/0245192 A1 | 11/2005 | Karabinis | |
| 2005/0260947 A1 | 11/2005 | Karabinis et al. | |
| 2005/0260984 A1 | 11/2005 | Karabinis | |
| 2005/0265273 A1 | 12/2005 | Karabinis et al. | |
| 2005/0272369 A1 | 12/2005 | Karabinis et al. | |
| 2005/0282542 A1 | 12/2005 | Karabinis | |
| 2005/0288011 A1 | 12/2005 | Dutta | |
| 2006/0040659 A1 | 2/2006 | Karabinis | |

FOREIGN PATENT DOCUMENTS

| | | |
|---|---|---|
| EP | 0 597 225 A1 | 5/1994 |
| EP | 0717577 A2 | 6/1996 |
| EP | 0 506 255 B1 | 11/1996 |

| | | |
|---|---|---|
| EP | 0 748 065 A2 | 12/1996 |
| EP | 0 755 163 A2 | 1/1997 |
| EP | 0 797 319 A2 | 9/1997 |
| EP | 0 926 844 | 6/1999 |
| EP | 0926844 A2 | 6/1999 |
| EP | 1 047 278 A2 | 10/2000 |
| WO | WO 01/54314 A1 | 7/2001 |
| WO | WO 02/03722 | 1/2002 |
| WO | WO 2002-03722 | 1/2002 |

OTHER PUBLICATIONS

PCT International Search Report PCT/US 03/12687.
Partial PCT Search for PCT/US 03/12687.

International Preliminary Examination Report, PCT/US02/24694, Apr. 9, 2003.

International Search Report, PCT/US02/24694, Dec. 10, 2002.

Global.com, "Globalstar Demonstrates World's First Prototype of Terrestrial System to Supplemental Satellite Phones," http://www.globalcomsatphone.com/globalcom/globalstar_terrestrial_system.html, Jul. 18, 2002, 2 pages.

Ayyagari et al., "A satellite-augmented cellular network concept", *Wireless Networks*, Vo. 4, 1998, pp. 189-198.

* cited by examiner

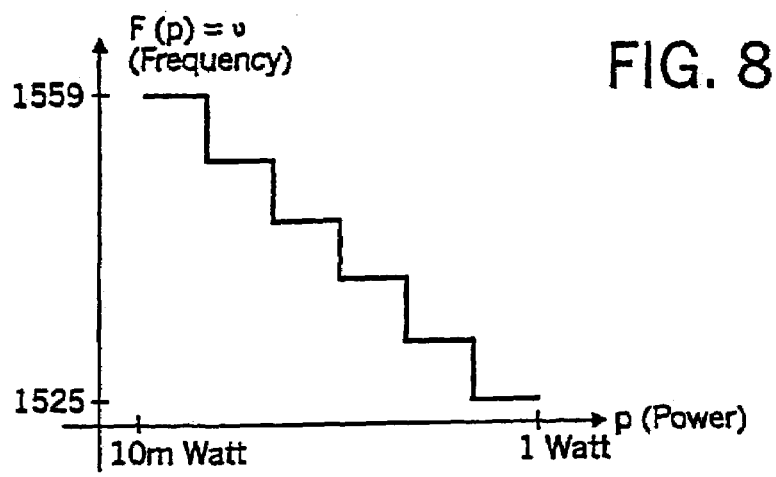
FIG. 8
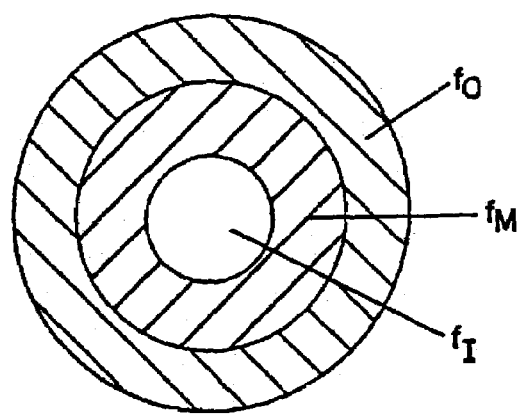
FIG. 9
FIG. 10
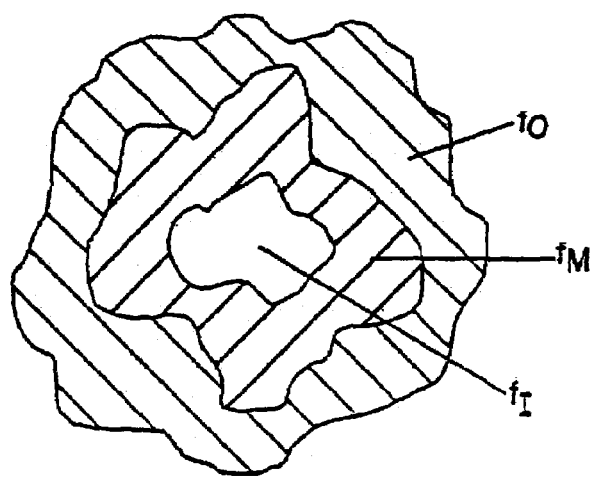

SATELLITE RADIOTELEPHONE SYSTEMS PROVIDING STAGGERED SECTORIZATION FOR TERRESTRIAL REUSE OF SATELLITE FREQUENCIES AND RELATED METHODS AND RADIOTELEPHONE SYSTEMS

CROSS-REFERENCE TO RELATED APPLICATIONS

This application claims the benefit of priority from provisional Application No. 60/393,287, filed Jul. 2, 2002, entitled Staggered Sectorization For Terrestrial Reuse Of Satellite Frequencies. This application also claims the benefit of priority as a continuation-in-part application from application Ser. No. 10/074,097, filed Feb. 12, 2002 now U.S. Pat. No. 6,684,057, entitled Systems and Methods for Terrestrial Reuse of Cellular Satellite Frequency Spectrum which claims the benefit of priority from provisional Application No. 60/322,240, filed Sep. 14, 2001, entitled Systems and Methods For Terrestrial Re-Use of Mobile Satellite Spectrum. This application also claims the benefit of priority as a continuation-in-part application from application Ser. No. 10/180,281, filed Jun. 26, 2002 now U.S. Pat. No. 6,999,720, entitled Spatial Guardbands for Terrestrial Reuse of Satellite Frequencies, which claims priority from Provisional Application No. 60/347,173, filed Jan. 9, 2002, entitled Spatial Guardbands for Terrestrial Reuse of Satellite Frequencies. All of these applications are assigned to the assignee of the present application, the disclosures of all of which are hereby incorporated herein by reference in their entirety as if set forth fully herein.

FIELD OF THE INVENTION

This invention relates to radiotelephone communications systems and methods, and more particularly to terrestrial cellular and satellite cellular radiotelephone communications systems and methods.

BACKGROUND OF THE INVENTION

Satellite radiotelephone communications systems and methods are widely used for radiotelephone communications. Satellite radiotelephone communications systems and methods generally employ at least one space-based component, such as one or more satellites that are configured to wirelessly communicate with a plurality of satellite radiotelephones.

A satellite radiotelephone communications system or method may utilize a single antenna beam covering an entire area served by the system. Alternatively, in cellular satellite radiotelephone communications systems and methods, multiple beams are provided, each of which can serve distinct geographical areas in the overall service region, to collectively serve an overall satellite footprint. Thus, a cellular architecture similar to that used in conventional terrestrial cellular radiotelephone systems and methods can be implemented in cellular satellite-based systems and methods. The satellite typically communicates with radiotelephones over a bidirectional communications pathway, with radiotelephone communication signals being communicated from the satellite to the radiotelephone over a downlink or forward link, and from the radiotelephone to the satellite over an uplink or return link.

The overall design and operation of cellular satellite radiotelephone systems and methods are well known to those having skill in the art, and need not be described further herein. Moreover, as used herein, the term "radiotelephone" includes cellular and/or satellite radiotelephones with or without a multi-line display; Personal Communications System (PCS) terminals that may combine a radiotelephone with data processing, facsimile and/or data communications capabilities; Personal Digital Assistants (PDA) that can include a radio frequency transceiver and a pager, Internet/intranet access, Web browser, organizer, calendar and/or a global positioning system (GPS) receiver; and/or conventional laptop and/or palmtop computers or other appliances, which include a radio frequency transceiver.

As is well known to those having skill in the art, terrestrial networks can enhance cellular satellite radiotelephone system availability, efficiency and/or economic viability by terrestrially reusing at least some of the frequency bands that are allocated to cellular satellite radiotelephone systems. In particular, it is known that it may be difficult for cellular satellite radiotelephone systems to reliably serve densely populated areas, because the satellite signal may be blocked by high-rise structures and/or may not penetrate into buildings. As a result, the satellite spectrum may be underutilized or unutilized in such areas. The use of terrestrial retransmission can reduce or eliminate this problem.

Moreover, the capacity of the overall system can be increased significantly by the introduction of terrestrial retransmission, since terrestrial frequency reuse can be much denser than that of a satellite-only system. In fact, capacity can be enhanced where it may be mostly needed, i.e., densely populated urban/industrial/commercial areas. As a result, the overall system can become much more economically viable, as it may be able to serve a much larger subscriber base. Finally, satellite radiotelephones for a satellite radiotelephone system having a terrestrial component within the same satellite frequency band and using substantially the same air interface for both terrestrial and satellite communications can be more cost effective and/or aesthetically appealing. Conventional dual band/dual mode alternatives, such as the well known Thuraya, Iridium and/or Globalstar dual mode satellite/terrestrial radiotelephone systems, may duplicate some components, which may lead to increased cost, size and/or weight of the radiotelephone.

One example of terrestrial reuse of satellite frequencies is described in U.S. Pat. No. 5,937,332 to the present inventor Karabinis entitled Satellite Telecommunications Repeaters and Retransmission Methods, the disclosure of which is hereby incorporated herein by reference in its entirety as if set forth fully herein. As described therein, satellite telecommunications repeaters are provided which receive, amplify, and locally retransmit the downlink signal received from a satellite thereby increasing the effective downlink margin in the vicinity of the satellite telecommunications repeaters and allowing an increase in the penetration of uplink and downlink signals into buildings, foliage, transportation vehicles, and other objects which can reduce link margin. Both portable and non-portable repeaters are provided. See the abstract of U.S. Pat. No. 5,937,332.

In view of the above discussion, there continues to be a need for systems and methods for terrestrial reuse of cellular satellite frequencies that can allow improved reliability, capacity, cost effectiveness and/or aesthetic appeal for cellular satellite radiotelephone systems, methods and/or satellite radiotelephones.

SUMMARY OF THE INVENTION

According to embodiments of the present invention, satellite radiotelephone systems can include a space-based component and a plurality of ancillary terrestrial components. The space-based component can be configured to provide wireless radiotelephone communications over a satellite radiotelephone frequency band. The plurality of ancillary terrestrial components can be configured to terrestrially reuse at least one of the satellite radiotelephone frequencies with at least some of the ancillary terrestrial components terrestrially reusing the at least one of the satellite radiotelephone frequencies in a staggered sectorization. The at least one satellite radiotelephone frequency can be used to provide radio downlinks from respective ancillary terrestrial components to receiving radiotelephones.

In addition, the space-based component can be configured to provide wireless radiotelephone communications for a coverage area including the plurality of ancillary terrestrial components using at least one satellite radiotelephone frequency other than the at least one of the satellite radiotelephone frequencies reused by the ancillary terrestrial components in the staggered sectorization. The space-based component can also be configured to provide a down-link to receiving radiotelephones in the coverage area using the at least one satellite radiotelephone frequency other than the at least one of the satellite radiotelephone frequencies reused by the ancillary terrestrial components in the staggered sectorization. The space-based component can be further configured to provide wireless radiotelephone communications for a second coverage area not including the plurality of ancillary terrestrial components reusing the at least one of the satellite radiotelephone frequencies, wherein the space-based component provides wireless radiotelephone communications for the second coverage area using the at least one of the satellite radiotelephone frequencies reused by the ancillary terrestrial components in the staggered sectorization.

At lease some of the ancillary terrestrial components can be divided into n directional sectors and the at least one of the satellite radiotelephone frequencies can be reused within the at least some of the ancillary terrestrial components so that an aggregate of radiated power transmitted by the at least some of the ancillary terrestrial components at the at least one of the satellite radiotelephone frequencies in any direction is no greater than approximately 1/n of a total radiated power transmitted by the at least some of the ancillary terrestrial components at the at least one of the satellite radiotelephone frequencies. Moreover, each of the ancillary terrestrial components can be divided into n directional sectors. More particularly, n can be 3 so that each of the ancillary terrestrial components comprises three 120° sectors. In addition, the plurality of ancillary terrestrial components can be divided into a plurality of reuse clusters with each reuse cluster having a common number of ancillary terrestrial components, and with each reuse cluster reusing the at least one of the satellite radiotelephone frequencies no more than once.

According to additional embodiments of the present invention, satellite radiotelephone systems can include a space-based component and a plurality of ancillary terrestrial components. The space-based component can be configured to provide wireless radiotelephone communications over a satellite radiotelephone frequency band. The plurality of ancillary terrestrial components can be grouped into clusters of ancillary terrestrial components with at least one ancillary terrestrial component of each cluster transmitting to a plurality of directional sectors, and the clusters can reuse a satellite radiotelephone frequency from the satellite radiotelephone frequency band in a single directional sector of a single ancillary terrestrial component of the respective cluster with a direction of the directional sectors reusing the satellite radiotelephone frequency being staggered. More particularly, the satellite radiotelephone frequency can be used to provide radio downlinks from respective ancillary terrestrial components to receiving radiotelephones.

The space-based component can be further configured to provide wireless radiotelephone communications for a coverage area including the plurality of ancillary terrestrial components using a satellite radiotelephone frequency other than satellite radiotelephone frequencies reused by the ancillary terrestrial components in the staggered directional sectors. More particularly, the space-based component can be configured to provide a down-link to receiving radiotelephones in the coverage area using the satellite radiotelephone frequency other than the satellite radiotelephone frequency reused by the ancillary terrestrial components in the staggered directional sectors. The space-based component can be further configured to provide wireless radiotelephone communications for a second coverage area not including the plurality of ancillary terrestrial components reusing the satellite radiotelephone frequency in the staggered directional sectors, wherein the space-based component provides wireless radiotelephone communications for the second coverage area using the satellite radiotelephone frequency reused by the ancillary terrestrial components in the staggered directional sectors.

In addition, the ancillary terrestrial components transmitting to a plurality of directional sectors can be divided into n directional sectors and the satellite radiotelephone frequency can be reused within the clusters so that an aggregate of radiated power transmitted by the plurality of ancillary terrestrial components of the clusters at the satellite radiotelephone frequency in any direction is no greater than approximately 1/n of a total radiated power transmitted by the ancillary terrestrial components of the clusters at the satellite radiotelephone frequency. More particularly, n can equal 3 so that the ancillary terrestrial components transmitting to a plurality of directional sectors includes three 120° sectors. The clusters can also have a common number of ancillary terrestrial components, with each cluster reusing the satellite radiotelephone frequency no more than once.

According to additional embodiments of the present invention, methods of operating satellite radiotelephone systems can include providing wireless radiotelephone communications from a space-based component over a satellite radiotelephone frequency band. At least one of the satellite radiotelephone frequencies can be reused in a staggered sectorization to provide radiotelephone communications from a plurality of ancillary terrestrial components. More particularly, the at least one satellite radiotelephone frequency can be used to provide radio downlinks in a staggered sectorization from respective ancillary terrestrial components to receiving radiotelephones.

In addition, providing wireless radiotelephone communications from the space-based component can further include providing wireless radiotelephone communications for a coverage area including the plurality of ancillary terrestrial components using at least one satellite radiotelephone frequency other than the at least one of the satellite radiotelephone frequencies reused by the ancillary terrestrial components in the staggered sectorization. Providing wireless radiotelephone communications from the space-based component can also include providing a down-link to receiving radiotelephones in the coverage area using the at least one satellite radiotelephone frequency other than the at least one of the satellite radiotelephone frequencies reused by the ancillary terrestrial components in the staggered sectorization. Moreover, providing wireless radiotelephone communications from the space-based component can also include providing wireless radiotelephone communications for a second coverage area not including the plurality of ancillary terrestrial components reusing the at least one of the satellite radiotelephone frequencies, wherein wireless radiotelephone communications for the second coverage area are provided by the space-based component using the at least one of the satellite radiotelephone frequencies reused by the ancillary terrestrial components in the staggered sectorization.

At least some of the ancillary terrestrial components can be divided into n directional sectors and the at least one of the satellite radiotelephone frequencies can be reused within the at least some of the ancillary terrestrial components so that an aggregate of radiated power transmitted by the at least some of the ancillary terrestrial components at the at least one of the satellite radiotelephone frequencies in any direction is no greater than approximately 1/n of a total radiated power transmitted by the at least some of the ancillary terrestrial components at the at least one of the satellite radiotelephone frequencies. In the alternative, each of the ancillary terrestrial components can be divided into n directional sectors and the at least one of the satellite radiotelephone frequencies can be reused within the plurality of ancillary terrestrial components so that an aggregate of radiated power transmitted by the plurality of ancillary terrestrial components at the at least one of the satellite radiotelephone frequencies in any direction is no greater than approximately 1/n of a total radiated power transmitted by the plurality of the ancillary terrestrial components at the at least one of the satellite radiotelephone frequencies.

More particularly, n can equal 3 so that each of the ancillary terrestrial components includes three 120° sectors. In addition, the plurality of ancillary terrestrial components can be divided into a plurality of reuse clusters with each reuse cluster having a common number of ancillary terrestrial components, and with each reuse cluster reusing the at least one of the satellite radiotelephone frequencies no more than once.

According to still additional embodiments of the present invention, methods of operating a satellite radiotelephone system can include providing wireless radiotelephone communications from a space-based component over a satellite radiotelephone frequency band. A satellite radiotelephone frequency from the satellite radiotelephone frequency band can be reused to provide radiotelephone communications from a plurality of ancillary terrestrial components with the plurality of ancillary terrestrial components being grouped into clusters of ancillary terrestrial components with at least one ancillary terrestrial component of each cluster transmitting to a plurality of directional sectors and with a direction of the directional sectors reusing the satellite radiotelephone frequency being staggered. The satellite radiotelephone frequency can be used to provide radio downlinks from respective ancillary terrestrial components to receiving radiotelephones.

Providing wireless radiotelephone communications from the space-based component can further include providing wireless radiotelephone communications for a coverage area including the plurality of ancillary terrestrial components using a satellite radiotelephone frequency other than the satellite radiotelephone frequency reused by the ancillary terrestrial components in the staggered directional sectors. More particularly, a down-link to receiving radiotelephones in the coverage area can be provided by the space-based component using the satellite radiotelephone frequency other than the satellite radiotelephone frequency reused by the clusters of ancillary terrestrial components. Providing wireless radiotelephone communications from the space-based component can also include providing wireless radiotelephone communications for a second coverage area not including the plurality of ancillary terrestrial components reusing the satellite radiotelephone frequency in the staggered directional sectors. More particularly wireless radiotelephone communications can be provided for the second coverage area by the space-based component using the satellite radiotelephone frequency reused by the ancillary terrestrial components in the staggered directional sectors.

In addition, each of the ancillary terrestrial components transmitting to a plurality of directional sectors can be divided into n directional sectors and the satellite radiotelephone frequency can be reused within the clusters of ancillary terrestrial components. Accordingly, an aggregate of radiated power transmitted by the clusters of ancillary terrestrial components at the satellite radiotelephone frequency in any direction can be no greater than approximately 1/n of a total radiated power transmitted by the clusters of the ancillary terrestrial components at the satellite radiotelephone frequency. More particularly, n can equal 3 so that the ancillary terrestrial components transmitting to a plurality of directional sectors include three 120° sectors. Moreover, each cluster can have a common number of ancillary terrestrial components, and each cluster can reuse the satellite radiotelephone frequency only once.

According to yet additional embodiments of the present invention, radiotelephone systems can include a plurality of terrestrial components grouped into clusters of terrestrial components. At least one terrestrial component of each cluster can transmit to a plurality of directional sectors, and a plurality of the clusters can reuse a radiotelephone frequency in a single directional sector of a single terrestrial component of the respective cluster. In addition, a direction of the directional sectors reusing the radiotelephone frequency can be staggered. The radiotelephone frequency can be used to provide radio downlinks from respective terrestrial components to receiving radiotelephones.

Each of the terrestrial components transmitting to a plurality of directional sectors can be divided into n directional sectors and the radiotelephone frequency can be reused within the clusters of terrestrial components so that an aggregate of radiated power transmitted by the clusters of terrestrial components at the radiotelephone frequency in any direction is no greater than approximately 1/n of a total radiated power transmitted by the clusters of terrestrial components at the radiotelephone frequency. More particularly, n can equal 3 so that each of the ancillary terrestrial components transmitting to a plurality of directional sectors can include three 120° sectors. Each cluster can also have a common number of terrestrial components with each cluster reusing the radiotelephone frequency only once. Moreover, the radiotelephone frequency reused by the plurality of clusters can be within a band of satellite frequencies transmitted by a space-based component.

According to more embodiments of the present invention, methods of operating a radiotelephone system can include reusing a radiotelephone frequency to provide radiotelephone communications from a plurality of terrestrial components. The plurality of terrestrial components can be grouped into clusters of terrestrial components with at least one terrestrial component of each cluster transmitting to a plurality of directional sectors. More particularly, a direction of the directional sectors reusing the radiotelephone frequency can be staggered. Moreover, the radiotelephone frequency can be used to provide radio downlinks from respective terrestrial components to receiving radiotelephones.

In addition, the terrestrial components transmitting to a plurality of directional sectors can be divided into n directional sectors and the radiotelephone frequency can be reused within the clusters of terrestrial components so that an aggregate of radiated power transmitted by the clusters of terrestrial components at the radiotelephone frequency in any direction is no greater than approximately 1/n of a total radiated power transmitted by the plurality of the terrestrial components at the radiotelephone frequency. For example, n can be 3 so that terrestrial components transmitting to a plurality of directional sectors comprises three 120° sectors. In addition, each cluster can have a common number of terrestrial components, and each cluster can reuse the radiotelephone frequency only once. The radiotelephone frequency reused by the plurality of clusters can also be within a band of satellite frequencies transmitted by a space-based component.

According to yet additional embodiments of the present invention, methods of providing communications can include reusing a radiotelephone frequency among a plurality of terrestrial components to provide radiotelephone communications for a plurality of mobile terminals. In addition, reuse of the radiotelephone frequency among the plurality of terrestrial components can be randomized.

Moreover, the plurality of terrestrial components can be grouped into clusters of terrestrial components with at least one terrestrial component of each cluster transmitting to a plurality of directional sectors wherein randomizing reuse of the radiotelephone frequency includes reusing the radiotelephone frequency in no more than one directional sector of a cluster of terrestrial components. Randomizing reuse of the radiotelephone frequency in no more than one directional sector of a cluster of terrestrial components can also include reusing the radiotelephone frequency so that a direction of the directional sectors reusing the radiotelephone frequency is staggered.

The radiotelephone frequency can be used to provide downlinks from respective terrestrial components to receiving radiotelephones. In addition, the radiotelephone frequency reused among the plurality of terrestrial components can be within a band of satellite frequencies transmitted by a space-based component.

According to still additional embodiments of the present invention, a communications system can include means for reusing a radiotelephone frequency among a plurality of terrestrial components to provide radiotelephone communications for a plurality of mobile terminals. The communications system can also include means for randomizing reuse of the radiotelephone frequency among the plurality of terrestrial components. In addition, the plurality of terrestrial components can be grouped into clusters of terrestrial components with at least one terrestrial component of each cluster transmitting to a plurality of directional sectors and the means for randomizing reuse of the radiotelephone frequency can include means for reusing the radiotelephone frequency in no more than one directional sector of a cluster of terrestrial components.

The means for randomizing reuse of the radiotelephone frequency in no more than one directional sector of a cluster of terrestrial components can include means for reusing the radiotelephone frequency so that a direction of the directional sectors reusing the radiotelephone frequency is staggered. In addition, the radiotelephone frequency can be used to provide downlinks from respective terrestrial components to receiving radiotelephones. The radiotelephone frequency reused among the plurality of terrestrial components can be within a band of satellite frequencies transmitted by a space-based component.

BRIEF DESCRIPTION OF THE DRAWINGS

FIG. 8 graphically illustrates mapping of monotonically decreasing power levels to frequencies according to embodiments of the present invention.

FIG. 9 illustrates an ideal cell that is mapped to three power regions and three associated carrier frequencies according to embodiments of the invention.

FIG. 10 depicts a realistic cell that is mapped to three power regions and three associated carrier frequencies according to embodiments of the invention.

DETAILED DESCRIPTION

The present invention now will be described more fully hereinafter with reference to the accompanying drawings, in which typical embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
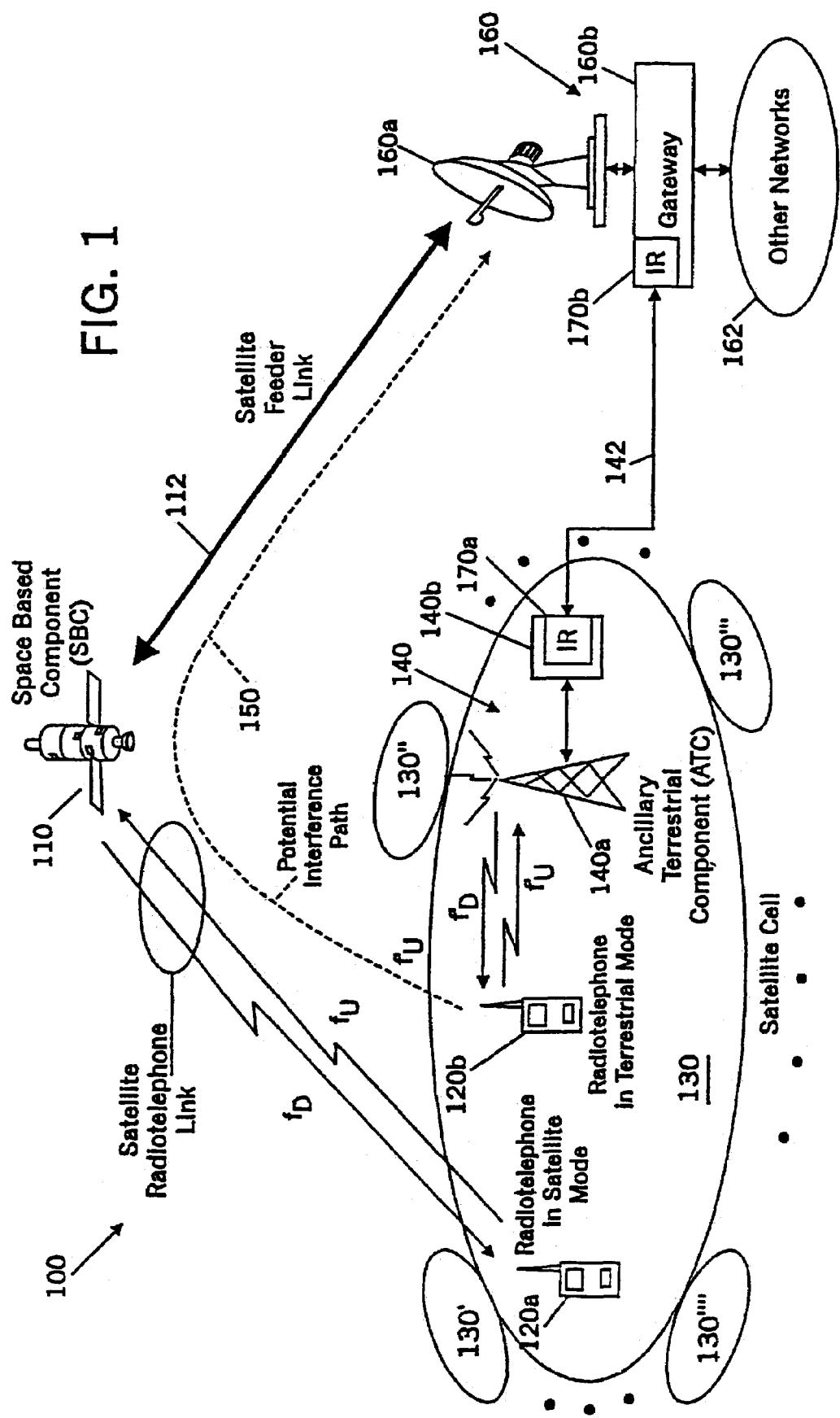
FIG. 1 is a schematic diagram of cellular radiotelephone systems and methods according to embodiments of the invention.

FIG. 1 is a schematic diagram of cellular satellite radiotelephone systems and methods according to embodiments of the invention. As shown in FIG. 1, these cellular satellite radiotelephone systems and methods 100 include at least one Space-Based Component (SBC) 110, such as a satellite. The space-based component 110 is configured to transmit wireless communications to a plurality of radiotelephones 120a, 120b in a satellite footprint comprising one or more satellite radiotelephone cells 130–130'''' over one or more satellite radiotelephone forward link (downlink) frequencies $f_D$. The space-based component 110 is configured to receive wireless communications from, for example, a first radiotelephone 120a in the satellite radiotelephone cell 130 over a satellite radiotelephone return link (uplink) frequency $f_U$. An ancillary terrestrial network, comprising at least one ancillary terrestrial component 140, which may include an antenna 140a and an electronics system 140b (for example, at least one antenna 140a and at least one electronics system 140b), is configured to receive wireless communications from, for example, a second radiotelephone 120b in the radiotelephone cell 130 over the satellite radiotelephone uplink frequency, denoted $f'_U$, which may be the same as $f_U$. Thus, as illustrated in FIG. 1 radiotelephone 120a may be communicating with the space-based component 110 while radiotelephone 120b may be communicating with the ancillary terrestrial component 140. As shown in FIG. 1, the space-based component 110 also undesirably receives the wireless communications from the second radiotelephone 120b in the satellite radiotelephone cell 130 over the satellite radiotelephone frequency $f_U$ as interference. More specifically, a potential interference path is shown at 150. In this potential interference path 150, the return link signal of the second radiotelephone 120b at carrier frequency $f'_U$ interferes with satellite communications. This interference would generally be strongest when $f'_U=f_U$, because, in that case, the same return link frequency would be used for space-based component and ancillary terrestrial component communications over the same satellite radiotelephone cell, and no spatial discrimination between satellite radiotelephone cells would appear to exist.

Still referring to FIG. 1, embodiments of satellite radiotelephone systems/methods 100 can include at least one gateway 160 that can include an antenna 160a and an electronics system 160b that can be connected to other networks 162 including terrestrial and/or other radiotelephone networks. The gateway 160 also communicates with the space-based component 110 over a satellite feeder link 112. The gateway 160 also communicates with the ancillary terrestrial component 140, generally over a terrestrial link 142.

Still referring to FIG. 1, an Interference Reducer (IR) 170a also may be provided at least partially in the ancillary terrestrial component electronics system 140b. Alternatively or additionally, an interference reducer 170b may be provided at least partially in the gateway electronics system 160b. In yet other alternatives, the interference reducer may be provided at least partially in other components of the cellular satellite system/method 100 instead of or in addition to the interference reducer 170a and/or 170b. The interference reducer is responsive to the space-based component 110 and to the ancillary terrestrial component 140, and is configured to reduce the interference from the wireless communications that are received by the space-based component 110 and is at least partially generated by the second radiotelephone 120b in the satellite radiotelephone cell 130 over the satellite radiotelephone frequency $f_U$. The interference reducer 170a and/or 170b uses the wireless communications $f'_U$ that are intended for the ancillary terrestrial component 140 from the second radiotelephone 120b in the satellite radiotelephone cell 130 using the satellite radiotelephone frequency $f'_U$ to communicate with the ancillary terrestrial component 140.

In embodiments of the invention, as shown in FIG. 1, the ancillary terrestrial component 140 generally is closer to the first and second radiotelephones 120a and 120b, respectively, than is the space-based component 110, such that the wireless communications from the second radiotelephone 120b are received by the ancillary terrestrial component 140 prior to being received by the space-based component 110. The interference reducer 170a and/or 170b is configured to generate an interference cancellation signal comprising, for example, at least one delayed replica of the wireless communications from the second radiotelephone 120b that are received by the ancillary terrestrial component 140, and to subtract the delayed replica of the wireless communications from the second radiotelephone 120b that are received by the ancillary terrestrial component 140 from the wireless communications that are received from the space-based component 110. The interference reduction signal may be transmitted from the ancillary terrestrial component 140 to the gateway 160 over link 142 and/or using other conventional techniques.

Thus, adaptive interference reduction techniques may be used to at least partially cancel the interfering signal, so that the same, or other nearby, satellite radiotelephone uplink frequency can be used in a given cell for communications by radiotelephones 120 with the satellite 110 and with the ancillary terrestrial component 140. Accordingly, all frequencies that are assigned to a given cell 130 may be used for both radiotelephone 120 communications with the space-based component 110 and with the ancillary terrestrial component 140. Conventional systems may avoid terrestrial reuse of frequencies within a given satellite cell that are being used within the satellite cell for satellite communications. Stated differently, conventionally, only frequencies used by other satellite cells may be candidates for terrestrial reuse within a given satellite cell. Beam-to-beam spatial isolation that is provided by the satellite system was relied upon to reduce or minimize the level of interference from the terrestrial operations into the satellite operations. In sharp contrast, embodiments of the invention can use an interference reducer to allow all frequencies assigned to a satellite cell to be used terrestrially and for satellite radiotelephone communications.

Embodiments of the invention according to FIG. 1 may arise from a realization that the return link signal from the second radiotelephone 120b at $f_U$ generally will be received and processed by the ancillary terrestrial component 140 much earlier relative to the time when it will arrive at the satellite gateway 160 from the space-based component 110 via the interference path 150. Accordingly, the interference signal at the satellite gateway 160b can be at least partially canceled. Thus, as shown in FIG. 1, an interference cancellation signal, such as the demodulated ancillary terrestrial component signal, can be sent to the satellite gateway 160b by the interference reducer 170a in the ancillary terrestrial component 140, for example using link 142. In the interference reducer 170b at the gateway 160b, a weighted (in amplitude and/or phase) replica of the signal may be formed using, for example, adaptive transversal filter techniques that are well known to those having skill in the art. Then, a transversal filter output signal is subtracted from the aggregate received satellite signal at frequency $f_U$ that contains desired as well as interference signals. Thus, the interference cancellation need not degrade the signal-to-noise ratio of the desired signal at the gateway 160, because a regenerated (noise-free) terrestrial signal, for example as regenerated by the ancillary terrestrial component 140, can be used to perform interference suppression.

Figure 2:
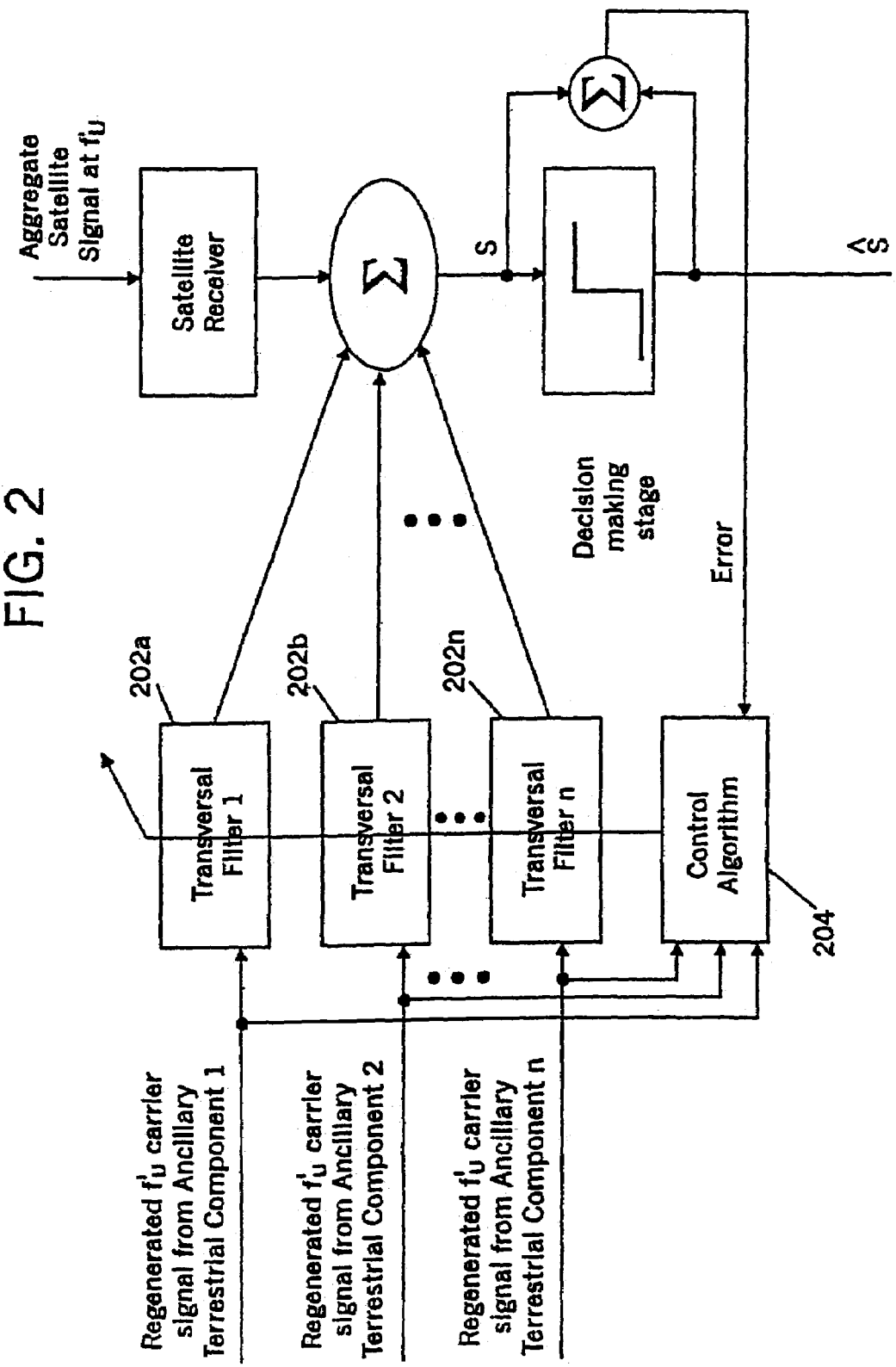
FIG. 2 is a block diagram of adaptive interference reducers according to embodiments of the present invention.

FIG. 2 is a block diagram of embodiments of adaptive interference cancellers that may be located in the ancillary terrestrial component 140, in the gateway 160, and/or in another component of the cellular radiotelephone system 100. As shown in FIG. 2, one,or more control algorithms 204, known to those having skill in the art, may be used to adaptively adjust the coefficients of a plurality of transversal filters 202a–202n. Adaptive algorithms, such as Least Mean Square Error (LMSE), Kalman, Fast Kalman, Zero Forcing and/or various combinations thereof or other techniques may be used. It will be understood by those having skill in the art that the architecture of FIG. 2 may be used with an LMSE algorithm. However, it also will be understood by those having skill in the art that conventional architectural modifications may be made to facilitate other control algorithms.

Figure 3:
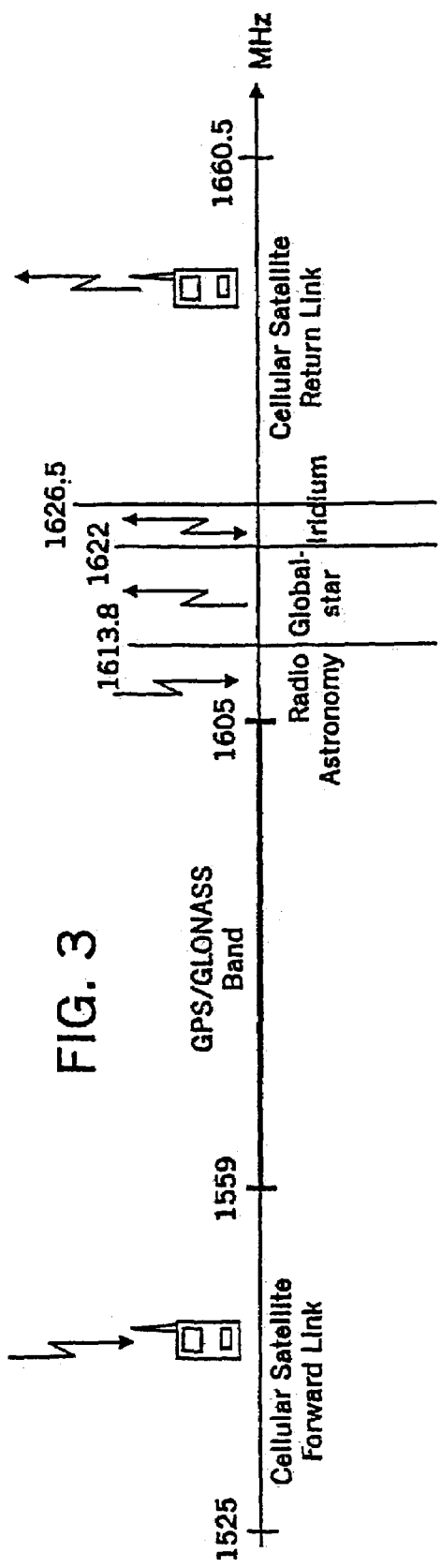
FIG. 3 is a spectrum diagram that illustrates satellite L-band frequency allocations.

Additional embodiments of the invention now will be described with reference to FIG. 3, which illustrates L-band frequency allocations including cellular radiotelephone system forward links and return links. As shown in FIG. 3, the space-to-ground L-band forward link (downlink) frequencies are assigned from 1525 MHz to 1559 MHz. The ground-to-space L-band return link (uplink) frequencies occupy the band from 1626.5 MHz to 1660.5 MHz. Between the forward and return L-band links lie the GPS/GLONASS radionavigation band (from 1559 MHz to 1605 MHz).

In the detailed description to follow, GPS/GLONASS will be referred to simply as GPS for the sake of brevity. Moreover, the acronyms ATC and SBC will be used for the ancillary terrestrial component and the space-based component, respectively, for the sake of brevity.

As is known to those skilled in the art, GPS receivers may be extremely sensitive since they are designed to operate on very weak spread-spectrum radionavigation signals that arrive on the earth from a GPS satellite constellation. As a result, GPS receivers may to be highly susceptible to in-band interference. ATCs that are configured to radiate L-band frequencies in the forward satellite band (1525 to 1559 MHz) can be designed with very sharp out-of-band emissions filters to satisfy the stringent out-of-band spurious emissions desires of GPS.

Referring again to FIG. 1, some embodiments of the invention can provide systems and methods that can allow an ATC 140 to configure itself in one of at least two modes. In accordance with a first mode, which may be a standard mode and may provide highest capacity, the ATC 140 transmits to the radiotelephones 120 over the frequency range from 1525 MHz to 1559 MHz, and receives transmissions from the radiotelephones 120 in the frequency range from 1626.5 MHz to 1660.5 MHz, as illustrated in FIG. 3. In contrast, in a second mode of operation, the ATC 140 transmits wireless communications to the radiotelephones 120 over a modified range of satellite band forward link (downlink) frequencies. The modified range of satellite band forward link frequencies may be selected to reduce, compared to the unmodified range of satellite band forward link frequencies, interference with wireless receivers such as GPS receivers that operate outside the range of satellite band forward link frequencies.

Many modified ranges of satellite band forward link frequencies may be provided according to embodiments of the present invention. In some embodiments, the modified range of satellite band forward link frequencies can be limited to a subset of the original range of satellite band forward link frequencies, so as to provide a guard band of unused satellite band forward link frequencies. In other embodiments, all of the satellite band forward link frequencies are used, but the wireless communications to the radiotelephones are modified in a manner to reduce interference with wireless receivers that operate outside the range of satellite band forward link frequencies. Combinations and subcombinations of these and/or other techniques also may be used, as will be described below.

It also will be understood that embodiments of the invention that will now be described in connection with FIGS. 4–12 will be described in terms of multiple mode ATCs 140 that can operate in a first standard mode using the standard forward and return links of FIG. 3, and in a second or alternate mode that uses a modified range of satellite band forward link frequencies and/or a modified range of satellite band return link frequencies. These multiple mode ATCs can operate in the second, non-standard mode, as long as desirable, and can be switched to standard mode otherwise. However, other embodiments of the present invention need not provide multiple mode ATCs but, rather, can provide ATCs that operate using the modified range of satellite band forward link and/or return link frequencies.

Embodiments of the invention now will be described, wherein an ATC operates with an SBC that is configured to receive wireless communications from radiotelephones over a first range of satellite band return link frequencies and to transmit wireless communications to the radiotelephones over a second range of satellite band forward link frequencies that is spaced apart from the first range. According to these embodiments, the ATC is configured to use at least one time division duplex frequency to transmit wireless communications to the radiotelephones and to receive wireless communications from the radiotelephones at different times. In particular, in some embodiments, the at least one time division duplex frequency that is used to transmit wireless communications to the radiotelephones and to receive wireless communications from the radiotelephones at different times, comprises a frame including a plurality of slots. At least a first one of the slots is used to transmit wireless communications to the radiotelephones and at least a second one of the slots is used to receive wireless communications from the radiotelephones. Thus, in some embodiments, the ATC transmits and receives, in Time Division Duplex (TDD) mode, using frequencies from 1626.5 MHz to 1660.5 MHz. In some embodiments, all ATCs across the entire network may have the stated configuration/reconfiguration flexibility. In other embodiments, only some ATCs may be reconfigurable.

Figure 5:
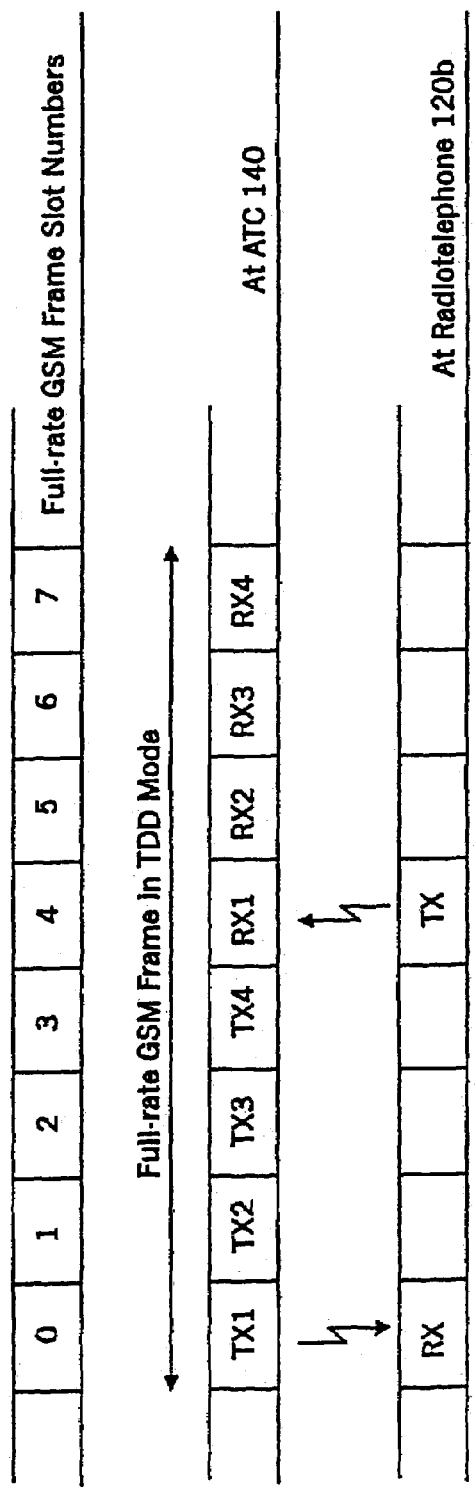
FIG. 5 illustrates time division duplex frame structures according to embodiments of the present invention.
Figure 4:
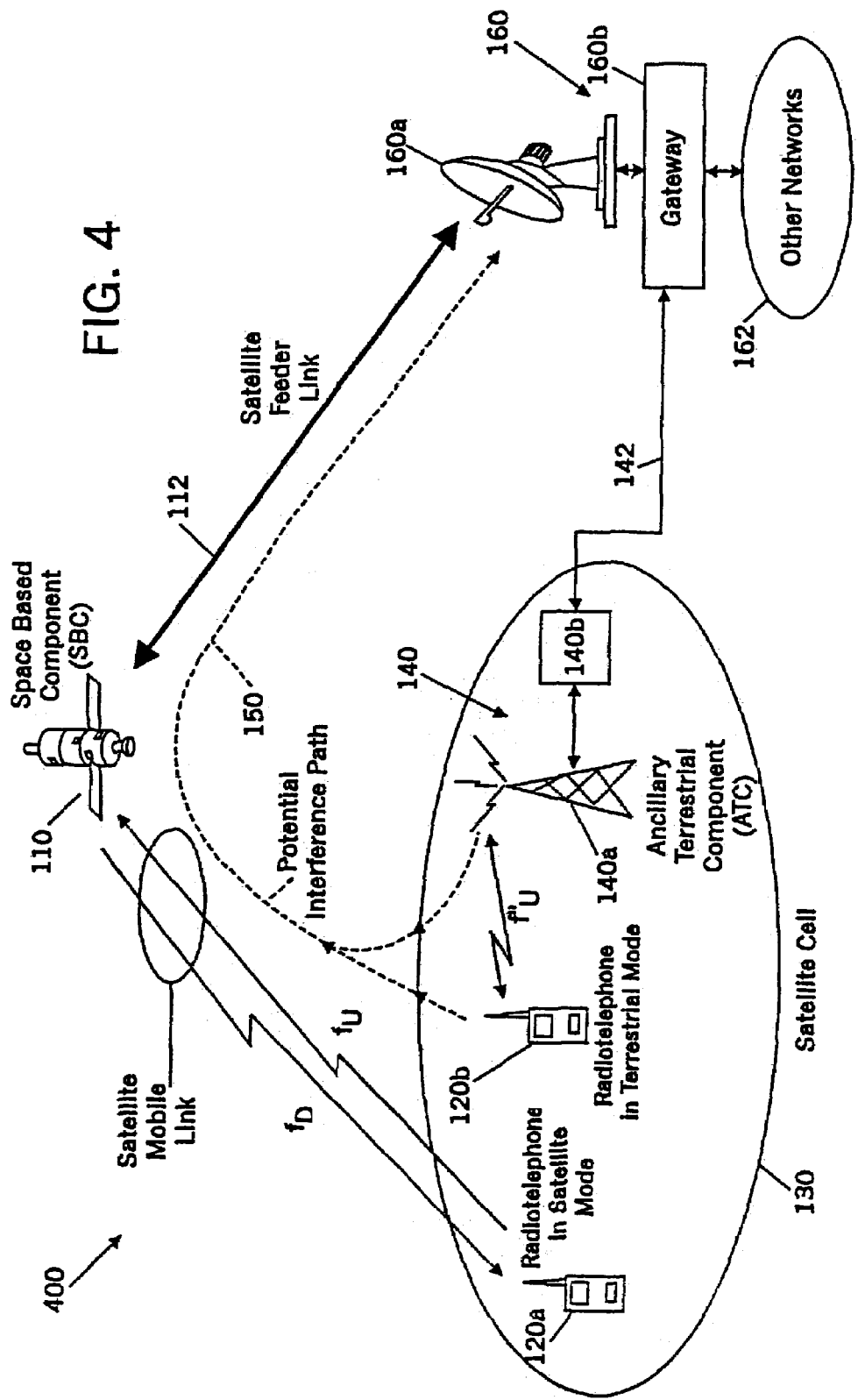
FIG. 4 is a schematic diagram of cellular satellite systems and methods according to other embodiments of the present invention.

FIG. 4 illustrates satellite systems and methods 400 according to some embodiments of the invention, including an ATC 140 communicating with a radiotelephone 120b using a carrier frequency $f''_U$ in TDD mode. FIG. 5 illustrates an embodiment of a TDD frame structure. Assuming full-rate GSM (eight time slots per frame), up to four full-duplex voice circuits can be supported by one TDD carrier. As shown in FIG. 5, the ATC 140 transmits to the radiotelephone 120b over, for example, time slot number 0. The radiotelephone 120b receives and replies back to the ATC 140 over, for example, time slot number 4. Time slots number 1 and 5 may be used to establish communications with another radiotelephone, and so on.

A Broadcast Control CHannel (BCCH) is preferably transmitted from the ATC 140 in standard mode, using a carrier frequency from below any guard band exclusion region. In other embodiments, a BCCH also can be defined using a TDD carrier. In any of these embodiments, radiotelephones in idle mode can, per established GSM methodology, monitor the BCCH and receive system-level and paging information. When a radiotelephone is paged, the system decides what type of resource to allocate to the radiotelephone in order to establish the communications link. Whatever type of resource is allocated for the radiotelephone communications channel (TDD mode or standard mode), the information is communicated to the radiotelephone, for example as part of the call initialization routine, and the radiotelephone configures itself appropriately.

It may be difficult for the TDD mode to co-exist with the standard mode over the same ATC, due, for example, to the ATC receiver LNA stage. In particular, assuming a mixture of standard and TDD mode GSM carriers over the same ATC, during the part of the frame when the TDD carriers are used to serve the forward link (when the ATC is transmitting TDD) enough energy may leak into the receiver front end of the same ATC to desensitize its LNA stage.

Techniques can be used to suppress the transmitted ATC energy over the 1600 MHz portion of the band from desensitizing the ATC's receiver LNA, and thereby allow mixed standard mode and TDD frames. For example, isolation between outbound and inbound ATC front ends and/or antenna system return loss may be increased or maximized. A switchable band-reject filter may be placed in front of the LNA stage. This filter would be switched in the receiver chain (prior to the LNA) during the part of the frame when the ATC is transmitting TDD, and switched out during the rest of the time. An adaptive interference canceller can be configured at RF (prior to the LNA stage). If such techniques are used, suppression of the order of 70 dB can be attained, which may allow mixed standard mode and TDD frames. However, the ATC complexity and/or cost may increase.

Thus, even though ATC LNA desensitization may be reduced or eliminated, it may use significant special engineering and attention and may not be economically worth the effort. Other embodiments, therefore, may keep TDD ATCs pure TDD, with the exception, perhaps, of the BCCH carrier which may not be used for traffic but only for broadcasting over the first part of the frame, consistent with TDD protocol. Moreover, Random Access CHannel (RACH) bursts may be timed so that they arrive at the ATC during the second half of the TDD frame. In some embodiments, all TDD ATCs may be equipped to enable reconfiguration in response to a command.

It is well recognized that during data communications or other applications, the forward link may use transmissions at higher rates than the return link. For example, in web browsing with a radiotelephone, mouse clicks and/or other user selections typically are transmitted from the radiotelephone to the system. The system, however, in response to a user selection, may have to send large data files to the radiotelephone. Hence, other embodiments of the invention may be configured to enable use of an increased or maximum number of time slots per forward GSM carrier frame, to provide a higher downlink data rate to the radiotelephones.

Thus, when a carrier frequency is configured to provide service in TDD mode, a decision may be made as to how many slots will be allocated to serving the forward link, and how many will be dedicated to the return link. Whatever the decision is, it may be desirable that it be adhered to by all TDD carriers used by the ATC, in order to reduce or avoid the LNA desensitization problem described earlier. In voice communications, the partition between forward and return link slots may be made in the middle of the frame as voice activity typically is statistically bidirectionally symmetrical. Hence, driven by voice, the center of the frame may be where the TDD partition is drawn.

To increase or maximize forward link throughput in data mode, data mode TDD carriers according to embodiments of the invention may use a more spectrally efficient modulation and/or protocol, such as the EDGE modulation and/or protocol, on the forward link slots. The return link slots may be based on a less spectrally efficient modulation and/or protocol such as the GPRS (GMSK) modulation and/or protocol. The EDGE modulation/protocol and the GPRS modulation/protocol are well known to those having skill in the art, and need not be described further herein. Given an EDGE forward/GPRS return TDD carrier strategy, up to (384/2)=192 kbps may be supported on the forward link while on the return link the radiotelephone may transmit at up to (115/2)≈64 kbps.

In other embodiments, it also is possible to allocate six time slots of an eight-slot frame for the forward link and only two for the return link. In these embodiments, for voice services, given the statistically symmetric nature of voice, the return link vocoder may need to be comparable with quarter-rate GSM, while the forward link vocoder can operate at full-rate GSM, to yield six full-duplex voice circuits per GSM TDD-mode carrier (a voice capacity penalty of 25%). Subject to this non-symmetrical partitioning strategy, data rates of up to (384)(6/8)=288 kbps may be achieved on the forward link, with up to (115) (2/8)≈32 kbps on the return link.

Figure 6:
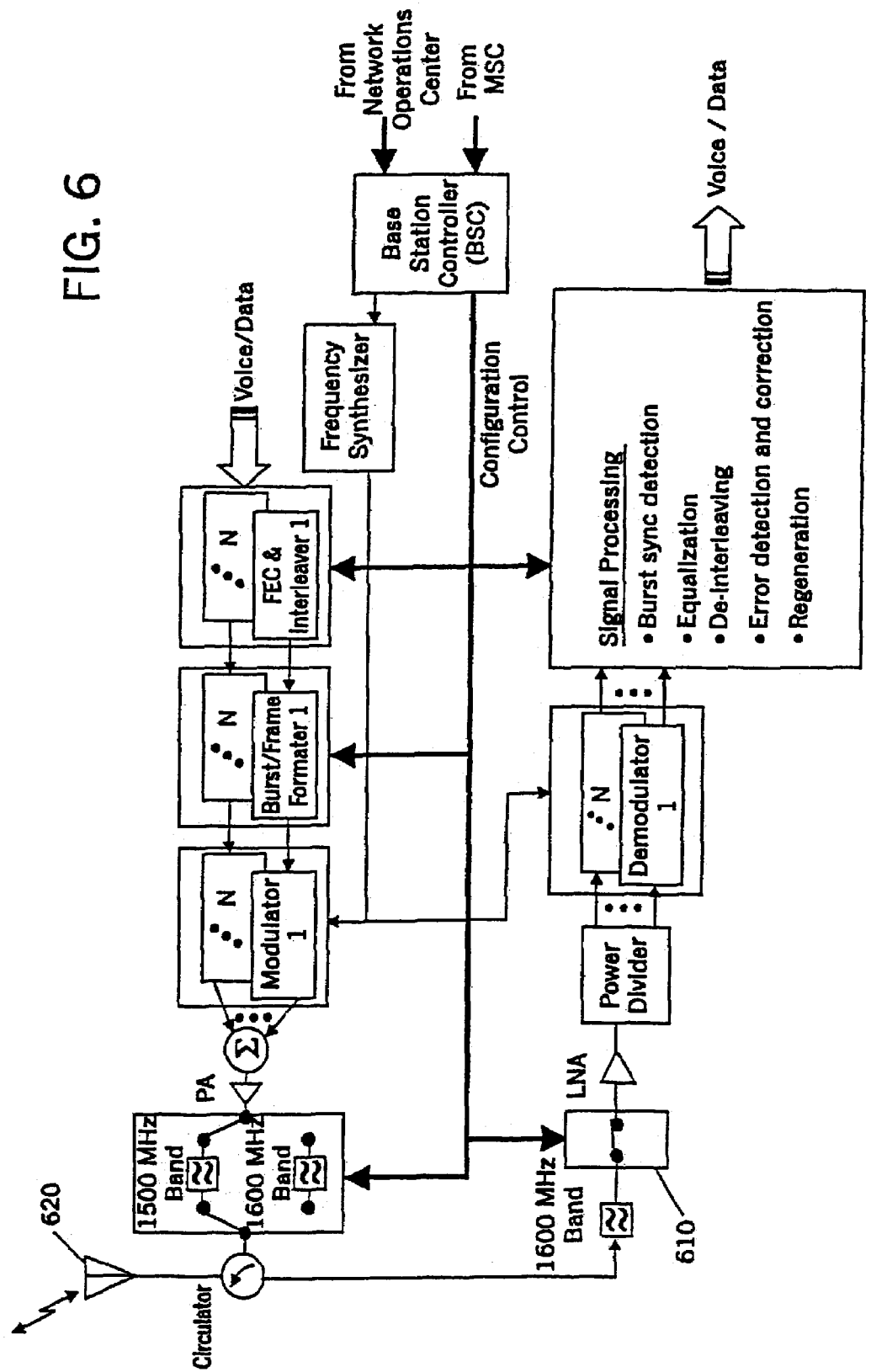
FIG. 6 is a block diagram of architectures of ancillary terrestrial components according to embodiments of the invention.

FIG. 6 depicts an ATC architecture according to embodiments of the invention, which can lend itself to automatic configuration between the two modes of standard GSM and TDD GSM on command, for example, from a Network Operations Center (NOC) via a Base Station Controller (BSC). It will be understood that in these embodiments, an antenna 620 can correspond to the antenna 140a of FIGS. 1 and 4, and the remainder of FIG. 6 can correspond to the electronics system 140b of FIGS. 1 and 4. If a reconfiguration command for a particular carrier, or set of carriers, occurs while the carrier(s) are active and are supporting traffic, then, via the in-band signaling Fast Associated Control CHannel (FACCH), all affected radiotelephones may be notified to also reconfigure themselves and/or switch over to new resources. If carrier(s) are reconfigured from TDD mode to standard mode, automatic reassignment of the carrier(s) to the appropriate standard-mode ATCs, based, for example, on capacity demand and/or reuse pattern can be initiated by the NOC. If, on the other hand, carrier(s) are reconfigured from standard mode to TDD mode, automatic reassignment to the appropriate TDD-mode ATCs can take place on command from the NOC.

Still referring to FIG. 6, a switch 610 may remain closed when carriers are to be demodulated in the standard mode. In TDD mode, this switch 610 may be open during the first half of the frame, when the ATC is transmitting, and closed during the second half of the frame, when the ATC is receiving. Other embodiments also may be provided.

FIG. 6 assumes N transceivers per ATC sector, where N can be as small as one, since a minimum of one carrier per sector generally is desired. Each transceiver is assumed to operate over one GSM carrier pair (when in standard mode) and can thus support up to eight full-duplex voice circuits, neglecting BCCH channel overhead. Moreover, a standard GSM carrier pair can support sixteen full-duplex voice circuits when in half-rate GSM mode, and up to thirty two full-duplex voice circuits when in quarter-rate GSM mode.

Figure 7:
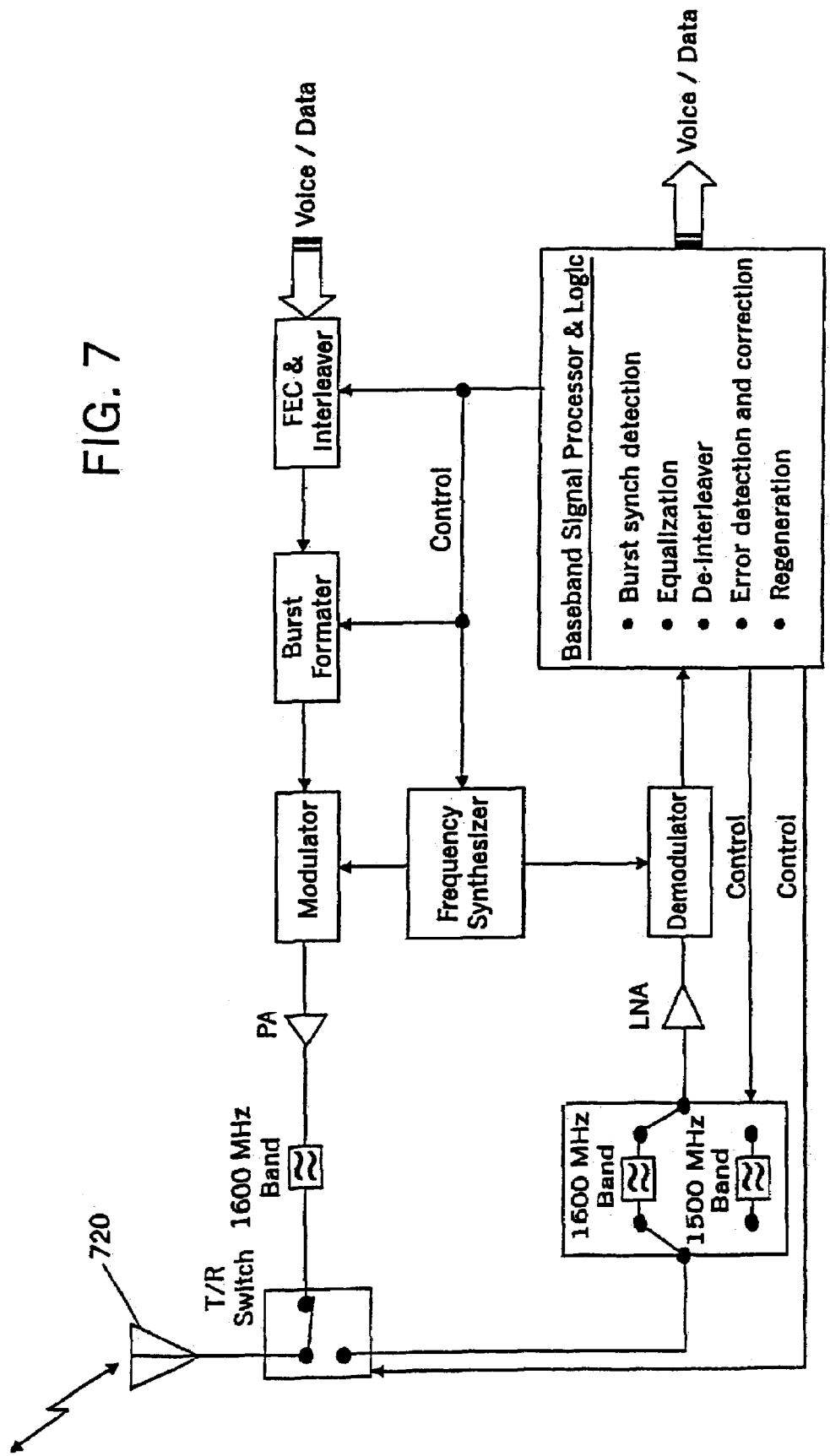
FIG. 7 is a block diagram of architectures of reconfigurable radiotelephones according to embodiments of the invention.

When in TDD mode, the number of full duplex voice circuits may be reduced by a factor of two, assuming the same vocoder. However, in TDD mode, voice service can be offered via the half-rate GSM vocoder with almost imperceptible quality degradation, in order to maintain invariant voice capacity. FIG. 7 is a block diagram of a reconfigurable radiotelephone architecture that can communicate with a reconfigurable ATC architecture of FIG. 6. In FIG. 7, an antenna 720 is provided, and the remainder of FIG. 7 can provide embodiments of an electronics system for the radiotelephone.

It will be understood that the ability to reconfigure ATCs and radiotelephones according to embodiments of the invention may be obtained at a relatively small increase in cost. The cost may be mostly in Non-Recurring Engineering (NRE) cost to develop software. Some recurring cost may also be incurred, however, in that at least an additional RF filter and a few electronically controlled switches may be used per ATC and radiotelephone. All other hardware/software can be common to standard-mode and TDD-mode GSM.

Referring now to FIG. 8, other radiotelephone systems and methods according to embodiments of the invention now will be described. In these embodiments, the modified second range of satellite band forward link frequencies includes a plurality of frequencies in the second range of satellite band forward link frequencies that are transmitted by the ATCs to the radiotelephones at a power level, such as maximum power level, that monotonically decreases as a function of (increasing) frequency. More specifically, as will be described below, in some embodiments, the modified second range of satellite band forward link frequencies includes a subset of frequencies proximate to a first or second end of the range of satellite band forward link frequencies that are transmitted by the ATC to the radiotelephones at a power level, such as a maximum power level, that monotonically decreases toward the first or second end of the second range of satellite band forward link frequencies. In still other embodiments, the first range of satellite band return link frequencies is contained in an L-band of satellite frequencies above GPS frequencies and the second range of satellite band forward link frequencies is contained in the L-band of satellite frequencies below the GPS frequencies. The modified second range of satellite band forward link frequencies includes a subset of frequencies proximate to an end of the second range of satellite band forward link frequencies adjacent the GPS frequencies that are transmitted by the ATC to the radiotelephones at a power level, such as a maximum power level, that monotonically decreases toward the end of the second range of satellite band forward link frequencies adjacent the GPS frequencies.

Without being bound by any theory of operation, a theoretical discussion of the mapping of ATC maximum power levels to carrier frequencies according to embodiments of the present invention now will be described. Referring to FIG. 8, let $v = \mathcal{F}(\rho)$ represent a mapping from the power ($\rho$) domain to the frequency ($v$) range. The power ($\rho$) is the power that an ATC uses or should transmit in order to reliably communicate with a given radiotelephone. This power may depend on many factors such as the radiotelephone's distance from the ATC, the blockage between the radiotelephone and the ATC, the level of multipath fading in the channel, etc., and as a result, will, in general, change as a function of time. Hence, the power used generally is determined adaptively (iteratively) via closed-loop power control, between the radiotelephone and ATC.

The frequency ($v$) is the satellite carrier frequency that the ATC uses to communicate with the radiotelephone. According to embodiments of the invention, the mapping $\mathcal{F}$ is a monotonically decreasing function of the independent variable $\rho$. Consequently, in some embodiments, as the maximum ATC power increases, the carrier frequency that the ATC uses to establish and/or maintain the communications link decreases. FIG. 8 illustrates an embodiment of a piecewise continuous monotonically decreasing (stair-case) function. Other monotonic functions may be used, including linear and/or nonlinear, constant and/or variable decreases. FACCH or Slow Associated Control CHannel (SACCH) messaging may be used in embodiments of the invention to facilitate the mapping adaptively and in substantially real time.

FIG. 9 depicts an ideal cell according to embodiments of the invention, where, for illustration purposes, three power regions and three associated carrier frequencies (or carrier frequency sets) are being used to partition a cell. For simplicity, one ATC transmitter at the center of the idealized cell is assumed with no sectorization. In embodiments of FIG. 9, the frequency (or frequency set) $f_I$ is taken from substantially the upper-most portion of the L-band forward link frequency set, for example from substantially close to 1559 MHz (see FIG. 3). Correspondingly, the frequency (or frequency set) $f_M$ is taken from substantially the central portion of the L-band forward link frequency set (see FIG. 3). In concert with the above, the frequency (or frequency set) $f_O$ is taken from substantially the lowest portion of the L-band forward link frequencies, for example close to 1525 MHz (see FIG. 3).

Thus, according to embodiments of FIG. 9, if a radiotelephone is being served within the outer-most ring of the cell, that radiotelephone is being served via frequency $f_o$. This radiotelephone, being within the furthest area from the ATC, has (presumably) requested maximum (or near maximum) power output from the ATC. In response to the maximum (or near maximum) output power request, the ATC uses its a priori knowledge of power-to-frequency mapping, such as a three-step staircase function of FIG. 9. Thus, the ATC serves the radiotelephone with a low-value frequency taken from the lowest portion of the mobile L-band forward link frequency set, for example, from as close to 1525 MHz as possible. This, then, can provide additional safeguard to any GPS receiver unit that may be in the vicinity of the ATC.

Embodiments of FIG. 9 may be regarded as idealized because they associate concentric ring areas with carrier frequencies (or carrier frequency sets) used by an ATC to serve its area. In reality, concentric ring areas generally will not be the case. For example, a radiotelephone can be close to the ATC that is serving it, but with significant blockage between the radiotelephone and the ATC due to a building. This radiotelephone, even though relatively close to the ATC, may also request maximum (or near maximum) output power from the ATC. With this in mind, FIG. 10 may depict a more realistic set of area contours that may be associated with the frequencies being used by the ATC to serve its territory, according to embodiments of the invention. The frequency (or frequency set) $f_I$ may be reused in the immediately adjacent ATC cells owing to the limited geographical span associated with $f_I$ relative to the distance between cell centers. This may also hold for $f_M$.

Figure 11:
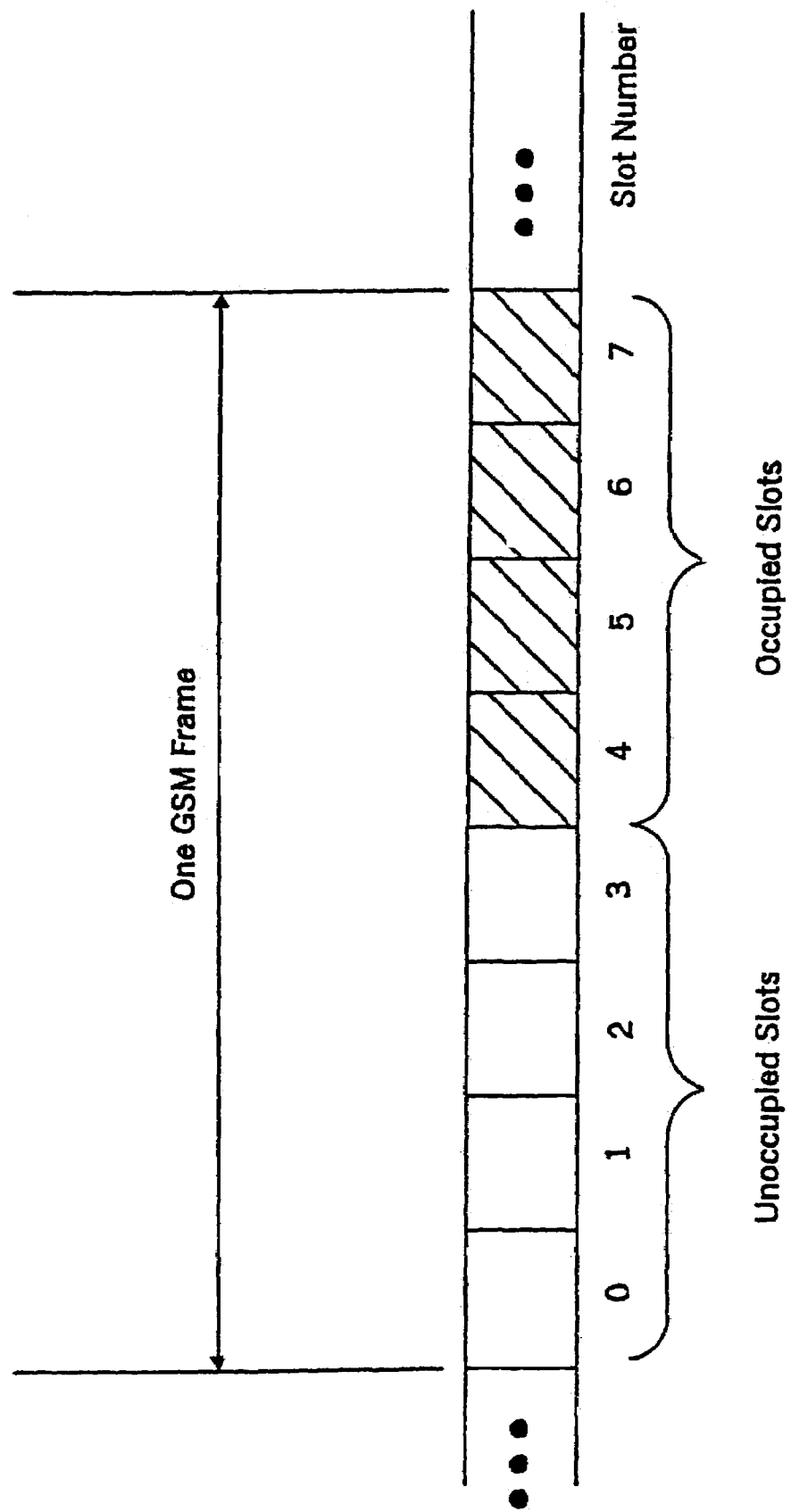
FIG. 11 illustrates two or more contiguous slots in a frame that are unoccupied according to embodiments of the present invention.

Referring now to FIG. 11, other modified second ranges of satellite band forward link frequencies that can be used by ATCs according to embodiments of the present invention now will be described. In these embodiments, at least one frequency in the modified second range of satellite band forward link frequencies that is transmitted by the ATC to the radiotelephones comprises a frame including a plurality of slots. In these embodiments, at least two contiguous slots in the frame that is transmitted by the ATC to the radiotelephones are left unoccupied. In other embodiments, three contiguous slots in the frame that is transmitted by the ATC to the radiotelephones are left unoccupied. In yet other embodiments, at least two contiguous slots in the frame that is transmitted by the ATC to the radiotelephones are transmitted at lower power than remaining slots in the frame. In still other embodiments, three contiguous slots in the frame that is transmitted by the ATC to the radiotelephones are transmitted at lower power than remaining slots in the frame. In yet other embodiments, the lower power slots may be used with first selected ones of the radiotelephones that are relatively close to the ATC and/or are experiencing relatively small signal blockage, and the remaining slots are transmitted at higher power to second selected ones of the radiotelephones that are relatively far from the ATC and/or are experiencing relatively high signal blockage.

Stated differently, in accordance with some embodiments of the invention, only a portion of the TDMA frame is utilized. For example, only the first four (or last four, or any contiguous four) time slots of a full-rate GSM frame are used to support traffic. The remaining slots are left unoccupied (empty). In these embodiments, capacity may be lost. However, as has been described previously, for voice services, half-rate and even quarter-rate GSM may be invoked to gain capacity back, with some potential degradation in voice quality. The slots that are not utilized preferably are contiguous, such as slots 0 through 3 or 4 through 7 (or 2 through 5, etc.). The use of non-contiguous slots such as 0, 2, 4, and 6, for example, may be less desirable. FIG. 11 illustrates four slots (4-7) being used and four contiguous slots (0-3) being empty in a GSM frame.

It has been found experimentally, according to these embodiments of the invention, that GPS receivers can perform significantly better when the interval between interference bursts is increased or maximized. Without being bound by any theory of operation, this effect may be due to the relationship between the code repetition period of the GPS C/A code (1 msec.) and the GSM burst duration (about 0.577 msec.). With a GSM frame occupancy comprising alternate slots, each GPS signal code period can experience at least one "hit", whereas a GSM frame occupancy comprising four to five contiguous slots allows the GPS receiver to derive sufficient clean information so as to "flywheel" through the error events.

According to other embodiments of the invention, embodiments of FIGS. 8–10 can be combined with embodiments of FIG. 11. Furthermore, according to other embodiments of the invention, if an $f_f$ carrier of FIG. 9 or 10 is underutilized, because of the relatively small footprint of the inner-most region of the cell, it may be used to support additional traffic over the much larger outermost region of the cell.

Figure 12:
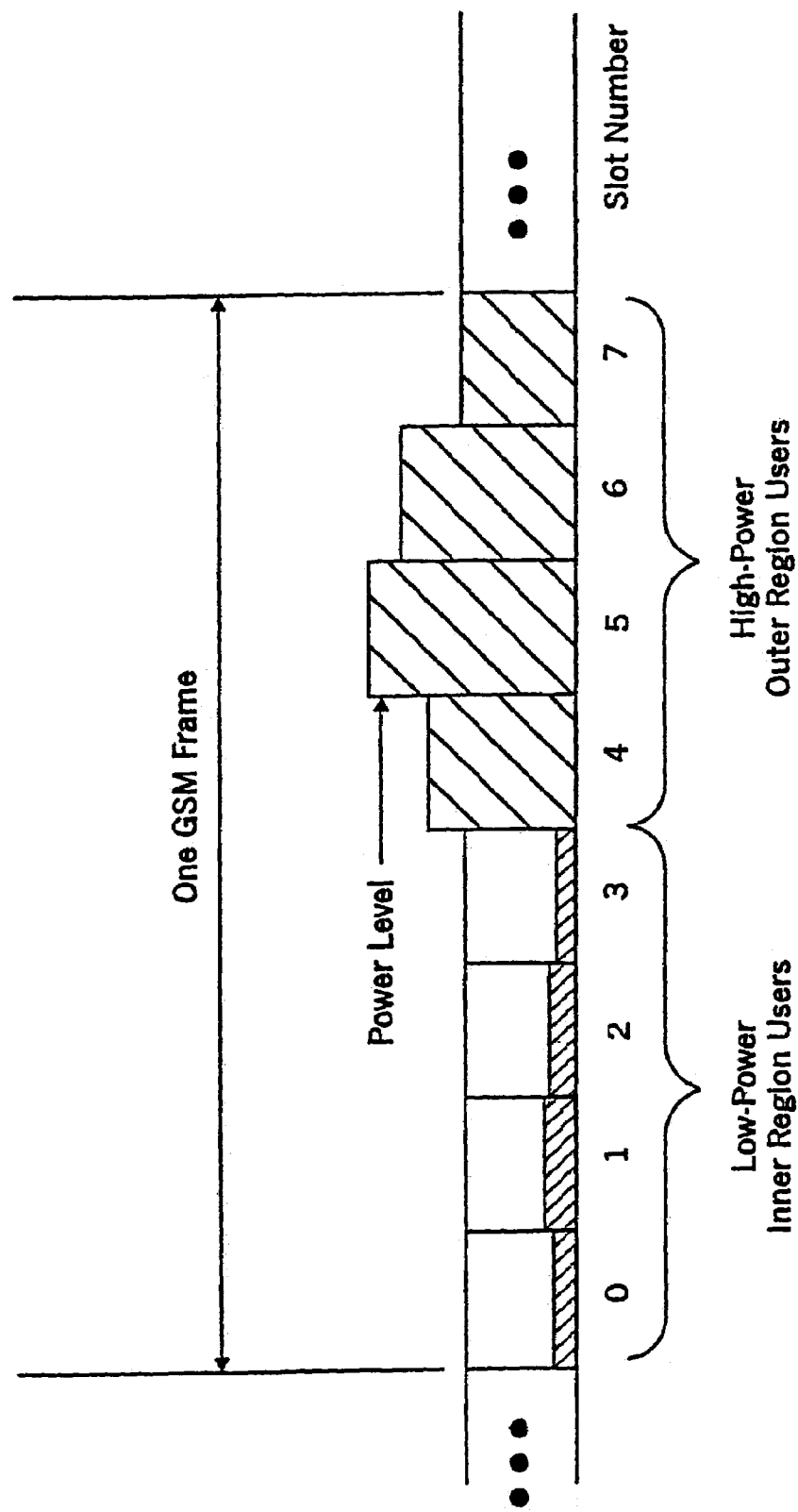
FIG. 12 illustrates loading of two or more contiguous slots with lower power transmissions according to embodiments of the present invention.

Thus, for example, assume that only the first four slots in each frame of $f_f$ are being used for inner region traffic. In embodiments of FIGS. 8–10, these four $f_f$ slots are carrying relatively low power bursts, for example of the order of 100 mW or less, and may, therefore, appear as (almost) unoccupied from an interference point of view. Loading the remaining four (contiguous) time slots of $f_f$ with relatively high-power bursts may have negligible effect on a GPS receiver because the GPS receiver would continue to operate reliably based on the benign contiguous time interval occupied by the four low-power GSM bursts. FIG. 12 illustrates embodiments of a frame at carrier $f_f$ supporting four low-power (inner interval) users and four high-power (outer interval) users. In fact, embodiments illustrated in FIG. 12 may be a preferred strategy for the set of available carrier frequencies that are closest to the GPS band. These embodiments may avoid undue capacity loss by more fully loading the carrier frequencies.

The experimental finding that interference from GSM carriers can be relatively benign to GPS receivers provided that no more than, for example, 5 slots per 8 slot GSM frame are used in a contiguous fashion can be very useful. It can be particularly useful since this experimental finding may hold even when the GSM carrier frequency is brought very close to the GPS band (as close as 1558.5 MHz) and the power level is set relatively high. For example, with five contiguous time slots per frame populated, the worst-case measured GPS receiver may attain at least 30 dB of desensitization margin, over the entire ATC service area, even when the ATC is radiating at 1558.5 MHz. With four contiguous time slots per frame populated, an additional 10 dB desensitization margin may be gained for a total of 40 dB for the worst-case measured GPS receiver, even when the ATC is radiating at 1558.5 MHz.

There still may be concern about the potential loss in network capacity (especially in data mode) that may be incurred over the frequency interval where embodiments of FIG. 11 are used to underpopulate the frame. Moreover, even though embodiments of FIG. 12 can avoid capacity loss by fully loading the carrier, they may do so subject to the constraint of filling up the frame with both low-power and high-power users. Moreover, if forward link carriers are limited to 5 contiguous high power slots per frame, the maximum forward link data rate per carrier that may be aimed at a particular user, may become proportionately less.

Therefore, in other embodiments, carriers which are subject to contiguous empty/low power slots are not used for the forward link. Instead, they are used for the return link. Consequently, in some embodiments, at least part of the ATC is configured in reverse frequency mode compared to the SBC in order to allow maximum data rates over the forward link throughout the entire network. On the reverse frequency return link, a radiotelephone may be limited to a maximum of 5 slots per frame, which can be adequate for the return link. Whether the five available time slots per frame, on a reverse frequency return link carrier, are assigned to one radiotelephone or to five different radiotelephones, they can be assigned contiguously in these embodiments. As was described in connection with FIG. 12, these five contiguous slots can be assigned to high-power users while the remaining three slots may be used to serve low-power users.

Other embodiments may be based on operating the ATC entirely in reverse frequency mode compared to the SBC. In these embodiments, an ATC transmits over the satellite return link frequencies while radiotelephones respond over the satellite forward link frequencies. If sufficient contiguous spectrum exists to support CDMA technologies, and in particular the emerging Wideband-CDMA 3G standard, the ATC forward link can be based on Wideband-CDMA to increase or maximize data throughput capabilities. Interference with GPS may not be an issue since the ATCs transmit over the satellite return link in these embodiments. Instead, interference may become a concern for the radiotelephones. Based, however, on embodiments of FIGS. 11–12, the radiotelephones can be configured to transmit GSM since ATC return link rates are expected, in any event, to be lower than those of the forward link. Accordingly, the ATC return link may employ GPRS-based data modes, possibly even EDGE. Thus, return link carriers that fall within a predetermined frequency interval from the GPS band-edge of 1559 MHz, can be under loaded, per embodiments of FIG. 11 or 12, to satisfy GPS interference concerns.

Finally, other embodiments may use a partial or total reverse frequency mode and may use CDMA on both forward and return links. In these embodiments, the ATC forward link to the radiotelephones utilizes the frequencies of the satellite return link (1626.5 MHz to 1660.5 MHz) whereas the ATC return link from the radiotelephones uses the frequencies of the satellite forward link (1525 MHz to 1559 MHz). The ATC forward link can be based on an existing or developing CDMA technology (e.g., IS-95, Wideband-CDMA, etc.). The ATC network return link can also be based on an existing or developing CDMA technology provided that the radiotelephone's output is gated to cease transmissions for approximately 3 msec once every T msec. In some embodiments, T will be greater than or equal to 6 msec.

This gating may not be needed for ATC return link carriers at approximately 1550 MHz or below. This gating can reduce or minimize out-of-band interference (desensitization) effects for GPS receivers in the vicinity of an ATC. To increase the benefit to GPS, the gating between all radiotelephones over an entire ATC service area can be substantially synchronized. Additional benefit to GPS may be derived from system-wide synchronization of gating. The ATCs can instruct all active radiotelephones regarding the gating epoch. All ATCs can be mutually synchronized via GPS.

Spatial Guardbands for Terrestrial Reuse of Satellite Frequencies

Some embodiments of the invention that were described above in connection with FIGS. 1–2 included interference reducers, to allow a satellite radiotelephone frequency to be reused terrestrially within the same satellite cell, while allowing intra-system interference to be reduced or eliminated. Embodiments of the invention that will now be described in connection with FIGS. 13 and 14 can allow a satellite radiotelephone frequency for a given satellite cell to be reused terrestrially outside the given satellite cell. Some embodiments provide a spatial guardband that is sufficiently large to reduce or prevent interference between the satellite frequencies that are used for space-based communications in the given satellite cell and reused terrestrially outside the given cell. In other embodiments, the spatial guardband may not need to be used, in whole or in part.

Spatial guardbands according to some embodiments of the invention may be provided by separating the ancillary terrestrial components in the ancillary terrestrial network that terrestrially reuse the same (or nearby) frequency or frequencies as the given satellite radiotelephone cell outside a given (predetermined) satellite radiotelephone cell, by a sufficient distance from the given satellite radiotelephone cell, such that signals are attenuated to some desired degree by the satellite's antenna pattern. For example, the signals are attenuated such that transmissions from the ancillary terrestrial components that radiate the frequency or frequencies that are used in the given satellite radiotelephone cell are sufficiently attenuated in the given satellite cell, so as to reduce or prevent (harmful) interference therewith.

By providing a spatial guardband, some terrestrial reuse of satellite frequencies may be obtained. Moreover, an interference reducer, such as the interference reducer of FIG. 1 or 2, may not need to be used. The complexity of the system therefore may be reduced. Alternatively, when interference reducers according to embodiments of the invention are used, a satellite radiotelephone frequency also can be used terrestrially within the very same satellite cell, with reduced or no interference, but at the potential expense of system complexity.

Qualitatively, embodiments of the present invention that provide a spatial guardband for terrestrial reuse of satellite frequencies may use a predetermined frequency or set of frequencies for space-based communications within a given satellite radiotelephone cell. According to these embodiments, this frequency or set of frequencies is not reused terrestrially within the given satellite radiotelephone cell, by the ancillary terrestrial network. However, the ancillary terrestrial network that exists outside the given satellite radiotelephone cell can reuse this frequency or set of frequencies, as long as a spatial guardband is maintained around the given satellite radiotelephone cell that uses this frequency or set of frequencies for space-based communications.

Figure 13:
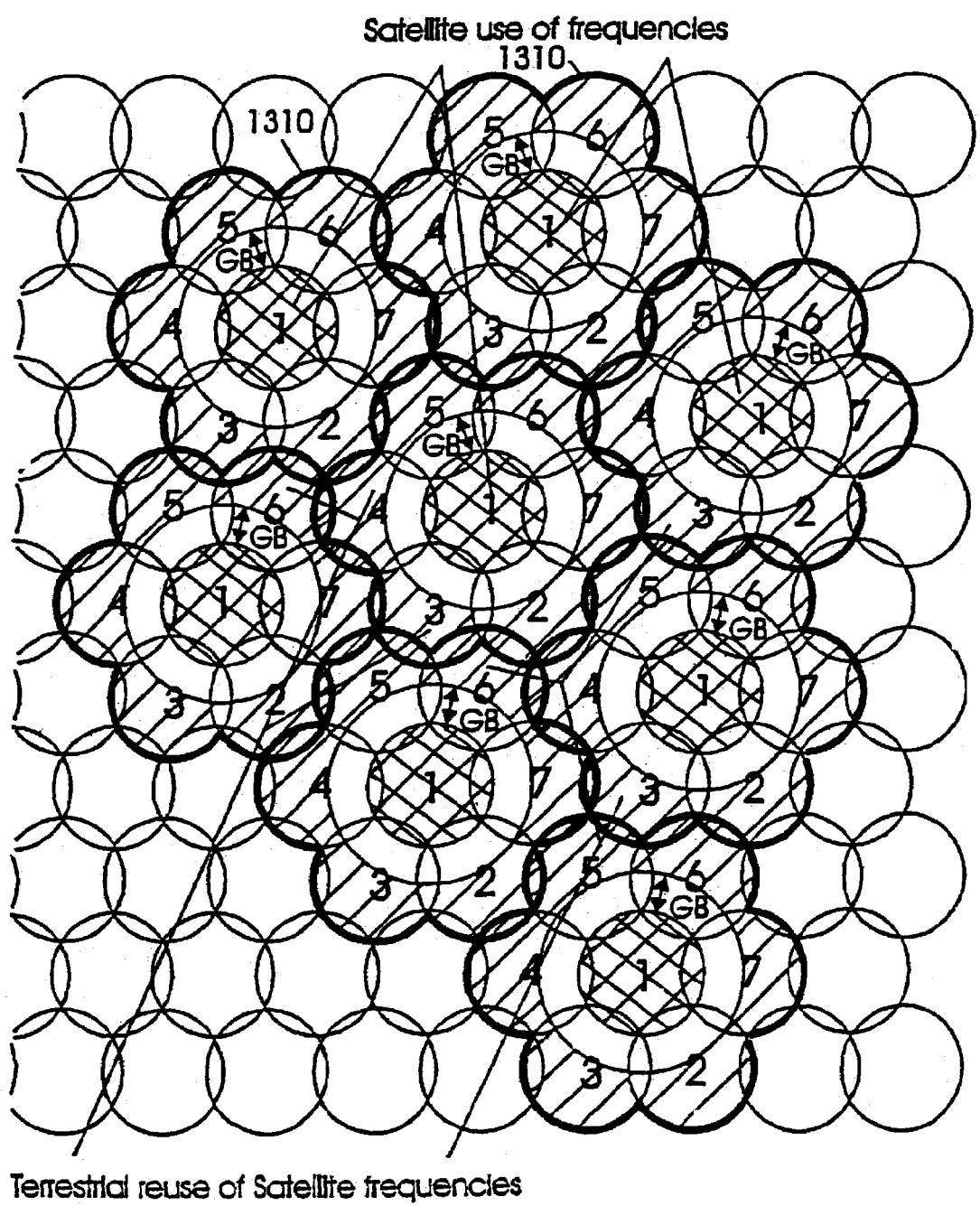
FIGS. 13 and 14 schematically illustrate spatial guardbands for terrestrial reuse of satellite frequencies in 7 and 9 cell frequency reuse patterns, respectively.

FIG. 13 is a schematic diagram of a satellite cellular radiotelephone system that uses a seven-cell frequency reuse pattern, wherein an ancillary terrestrial network reuses the satellite frequencies with the provision of a spatial guardband. Thus, FIG. 13 illustrates a seven-cell frequency reuse pattern 1310, outlined in a thick line, with satellite cells 1–7 contained within the seven-cell frequency reuse pattern. Although only eight repetitions of the frequency reuse plan 1310 are shown in FIG. 13, fewer or more repetitions may be used.

As is well known to those having skill in the art, a satellite cell, such as cells 1–7 of FIG. 13, may have a diameter that is on the order of hundreds of kilometers. In sharp contrast, a terrestrial network cell, such as a cell of an ancillary terrestrial network, may have a cell diameter that is on the order of ten kilometers or less. Thus, within a given satellite cell, such as a satellite cell 1–7 of FIG. 13, on the order of hundreds or thousands of ancillary terrestrial network cells may be present. As was shown in FIG. 1, each ancillary terrestrial network cell may include at least one ancillary terrestrial component (e.g., a base station tower with associate electronics).

According to some embodiments of the invention, selected ones of the ancillary terrestrial network cells outside a given satellite radiotelephone cell, such as cell 1 of FIG. 13, may terrestrially reuse the frequency or frequencies that are used by the given satellite radiotelephone cell 1, as long as those ancillary terrestrial network cells are spatially separated from the given satellite cell 1 by a guardband GB of FIG. 13 which is sufficiently large to reduce or prevent interference with the same frequency or frequencies that are also used in the given satellite radiotelephone cell 1. Although the guardband GB of FIG. 13 is shown as a symmetrical ring, real-world guardbands may have an irregular shape to account for the actual satellite antenna patterns which may intentionally or unintentionally deviate from those shown in FIG. 13.

Thus, as shown in FIG. 13 by the hatched area outside the satellite radiotelephone cells 1, ancillary terrestrial components within the ancillary terrestrial network in the hatched portions of satellite radiotelephone cells 2–7 can include an electronics system associated therewith, which can be configured to terrestrially reuse the same satellite frequency or frequencies used by cell 1, as long as a sufficient spatial guardband, shown by the unhatched areas of FIG. 13, is maintained between satellite cells 1 and the ancillary terrestrial components that terrestrially reuse these frequencies. The guardband may be on the order of half the radius of a satellite cell in width, but may vary based upon the actual design of the system. Stated differently, a given frequency or set of frequencies may be used throughout the hatched and cross-hatched area of FIG. 13, with the frequencies being used for space-based communications in the cross-hatched portions, corresponding to satellite cells 1, and also reused terrestrially in the hatched portions of the ancillary terrestrial network that are spatially separated from the satellite cells 1 by the guardband GB.

It will be understood by those having skill in the art that similar terrestrial reuse of satellite frequencies with spatial guardbands may be provided for the frequency or frequencies that are used in each of the remaining satellite cells 2–7. Terrestrial reuse with a spatial guardband for cells 2–7 are not shown in FIG. 13 for the sake of clarity.

Figure 14:
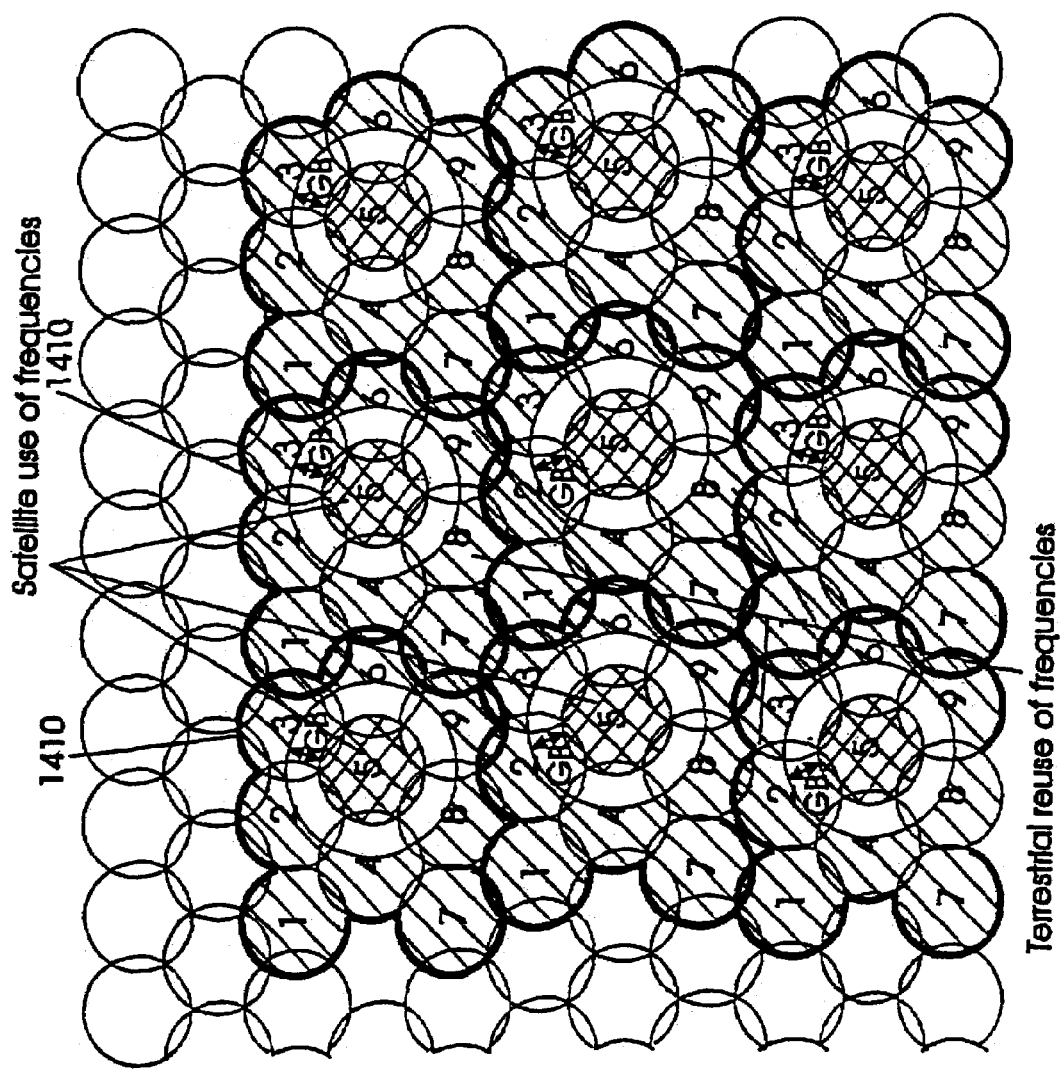

FIG. 14 illustrates other examples of terrestrial reuse of satellite frequencies using spatial guardbands according to some embodiments of the invention. In FIG. 14, a nine-cell frequency reuse pattern 1410 is shown for satellite radiotelephone cells 1–9. As also shown in FIG. 14, the frequency or frequencies that are used by a given satellite radiotelephone cell, for example cells 5, may be reused in the ancillary terrestrial network that overlaps with the remaining satellite cells 1–4 and 6–9, as long as a sufficient guardband GB is maintained, to reduce or prevent interference. As was the case for FIG. 13, terrestrial reuse of satellite frequencies with a spatial guardband is only shown for the frequency or frequencies used in satellite cells 5. The frequencies for the remaining satellite cells 1–4 and 6–9 also may be reused terrestrially in a similar manner, but are not shown in FIG. 14 for the sake of clarity.

As was described above, in some embodiments of the present invention, an ancillary terrestrial network is configured to terrestrially reuse at least one of the satellite radiotelephone frequencies that is used in a predetermined satellite cell in the satellite footprint, outside the predetermined satellite cell and separated therefrom by a spatial guardband. In some embodiments, when the ancillary terrestrial network comprises a plurality of ancillary terrestrial components, at least a first one of the ancillary terrestrial components that is located in the predetermined satellite cell is configured not to terrestrially reuse the at least one of the satellite radiotelephone frequencies that is used in the predetermined satellite cell, and at least a second of the ancillary terrestrial components that is located outside the predetermined satellite cell and separated therefrom by the spatial guardband, is configured to terrestrially reuse the at least one of the satellite radiotelephone frequencies that is used in the predetermined satellite cell. Accordingly, it may be desirable to determine, for each ancillary terrestrial component, whether the ancillary terrestrial component is located outside the predetermined satellite cell and separated therefrom by a spatial guardband.

In some embodiments of the invention, this determination may be made, for example at the time of setup of the ancillary terrestrial component, based on the geographic location thereof. Moreover, the determination also may be updated or changed by receiving a message at the ancillary terrestrial component that indicates that its location relative to the predetermined satellite cell has changed. This update may be used, for example, when the location of the satellite cells in the satellite footprint changes.

It may be difficult and/or time consuming to determine the boundaries (signal strength contours) of the spatial guardband regions with sufficient accuracy.

Moreover, the satellite antenna pattern may drift over time. Also, the satellite antenna pattern may be reconfigured periodically. Accordingly, other embodiments of the present invention may be configured to determine portions of the ancillary terrestrial network that are located outside the predetermined satellite cell and separated therefrom by a spatial guardband. In some embodiments, this determination may be made by receiving and/or processing at least one of the satellite radiotelephone frequencies of the satellite telephone frequency band. In still other embodiments, the satellite telephone frequencies include a plurality of Broadcast Control CHannel (BCCH) frequencies, and the determination is made by receiving and/or processing signal strength and/or content of at least one of the BCCH frequencies.

In still other embodiments, the ancillary terrestrial network comprises a plurality of ancillary terrestrial components. In some embodiments, each of these ancillary terrestrial components can be configured to determine whether it is located outside the predetermined satellite cell and separated therefrom by the spatial guardband. Moreover, in other embodiments, not every ancillary terrestrial component needs to determine whether it is located outside the predetermined satellite cell and separated therefrom by the spatial guardband. Rather, in these embodiments, at least one of the ancillary terrestrial components is configured to determine whether it is located outside the predetermined satellite cell and separated therefrom by a spatial guardband, and to transmit results of this determination to at least a second one of the plurality of ancillary terrestrial components. Accordingly, the ancillary terrestrial components can determine the satellite band frequencies that they may deploy.

More specifically, an ancillary terrestrial component may be equipped to receive the BCCH carrier frequencies that the satellite system is radiating. For example, for a seven cell frequency reuse pattern such as illustrated in FIG. 13, seven distinct carrier frequencies may be used by the satellite system for BCCH transmissions. These frequencies may be known a priori by the ancillary terrestrial network. The ancillary terrestrial components may be configured to receive and demodulate the BCCH carrier frequencies either simultaneously or sequentially.

Each satellite BCCH carrier, corresponding to a particular satellite cell, may contain information revealing frequencies (carriers) that the satellite cell is using for communications traffic. The satellite BCCH carrier also may carry information revealing the total set of frequencies available to the satellite system, as well as the frequency sets available for communications to other neighboring cells corresponding to the carriers used for BCCH transmission by the other neighboring (adjacent) satellite cells.

According to some embodiments of the present invention, since the ancillary terrestrial component is able to receive and demodulate the BCCH carrier frequencies used by the satellite system, it can determine the relative strengths of the received satellite BCCH carriers and the set of frequencies assigned for communications corresponding to each received BCCH carrier. Thus, with real time knowledge of the satellite system state and the received BCCH carrier strengths, an ancillary terrestrial component may not need to obtain additional information regarding its own position relative to any one spatial guardband and the associated boundaries (signal strength contours) thereof.

It will be understood by those having skill in the art that the area that may be spanned by ancillary terrestrial components generally may be relatively small compared to the regions spanned by satellite cells and/or spatial guardbands, in some embodiments. As such, according to other embodiments of the present invention, not every ancillary terrestrial component may need to be equipped with the satellite BCCH reception. In particular, only one or a few ancillary terrestrial components per satellite cell may need to detect the satellite BCCH. In fact, the detection of the satellite BCCH carrier frequencies may not even be collocated with any ancillary terrestrial component. Thus, only one or a subset of the ancillary terrestrial components that provide service to a geographical area may need to determine the frequency set that it may use for communications, and then can transmit this information to other ancillary terrestrial components serving the geographic area.

In some embodiments, in response to the received signal levels and/or the information content of the satellite BCCH carriers, the ancillary terrestrial component serving a given geographic area, or a subset of the ancillary terrestrial components, can determine the satellite band frequencies that they may deploy with reduced or minimum interference impact to the satellite communications. In some embodiments, satellite band frequencies that are associated with the weakest satellite BCCH carrier that is received, may be deployed by the ancillary terrestrial components with highest priority, followed by those corresponding to the next weakest BCCH carrier, etc. Thus, the entire ancillary terrestrial network that may be serving a particular geographic area may configure and reconfigure its frequency plan and, in some embodiments, in real time, in response to monitoring of the satellite network BCCH emissions.

Embodiments of the invention as illustrated, for example, in FIGS. 13 and 14 can terrestrially reuse satellite frequencies over much of the ancillary terrestrial network, and some embodiments can rely on spatial guardbands to reduce or prevent interference. Interference reducers, for example as shown in FIGS. 1–2, may not need to be used. However, it also will be understood that other embodiments may use a combination of terrestrial reuse using a spatial guardband and terrestrial reuse using an interference reducer over different portions of the satellite radiotelephone system footprint.

Accordingly, some embodiments of the invention can provide satellite radiotelephone systems and methods, wherein a space-based component is configured to receive wireless communications from radiotelephones in a satellite footprint over a satellite radiotelephone frequency band, and an ancillary terrestrial network also is configured to receive wireless communications from radiotelephones in the satellite footprint over the satellite radiotelephone frequency band. One or more frequencies used in a given satellite cell of the satellite footprint also are used by the ancillary terrestrial network that is outside the given satellite cell and, in some embodiments, that is separated from the given cell by a predetermined spatial guardband. Terrestrial reuse therefore may be provided over much of the satellite footprint, without creating excessive interference.

Staggered Sectorization for Terrestrial Reuse of Satellite Frequencies

According to some embodiments of the invention that were described above, satellite frequencies may be terrestrially reused, and various embodiments may be used for reducing, minimizing or eliminating interference by the terrestrially reused satellite frequencies with the satellite frequencies that are used for satellite communications. Embodiments of the present invention that will now be described can be used separately or in connection with any of the above-described embodiments, to allow further reduction, minimization or elimination of interference by terrestrially reused satellite frequencies. These embodiments also may be used in conventional cellular radiotelephone systems to reduce, minimize or eliminate interference with other radio systems.

Figure 15:
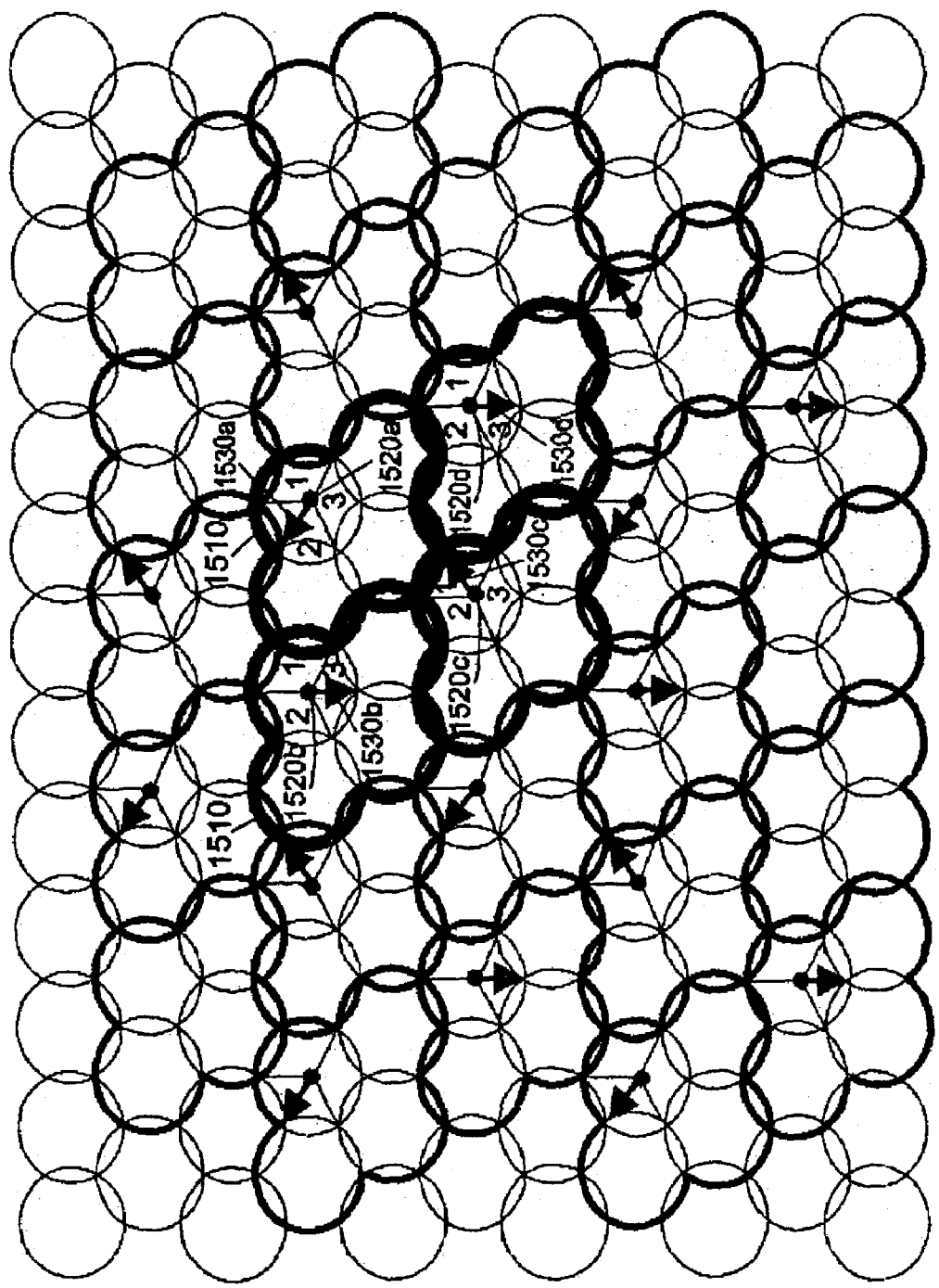
FIG. 15 schematically illustrates staggered sectorization for terrestrial reuse of satellite frequencies according to some embodiments of the present invention.

In particular, FIG. 15 illustrates a frequency reuse pattern by an ancillary terrestrial network comprising a network of ancillary terrestrial components (ATC). FIG. 15 may be contrasted with FIGS. 13 and 14, which illustrate satellite frequency reuse plans. Thus, in some embodiments, the network of ATCs shown in FIG. 15 may all be included within a satellite radiotelephone cell. In other embodiments, the network of ATCs may be spread over a plurality of satellite radiotelephone cells. It also will be understood that fewer or more ATCs may be used. Moreover, the network of ATCs shown in FIG. 15 may be used in the absence of a satellite radiotelephone cell.

FIG. 15 illustrates an ancillary terrestrial network of ATCs that uses a four-cell frequency reuse pattern, wherein the ancillary terrestrial network reuses the satellite frequencies that are used in a geographically overlapping and/or non-geographically overlapping satellite radiotelephone cell. It will be understood that, although FIG. 15 illustrates a four-cell frequency reuse pattern 1510, smaller or larger cell frequency reuse patterns may be used. The four-cell frequency reuse pattern 1510 is outlined in a thick line in FIG. 15.

As also shown in FIG. 15, each ATC may distribute its terrestrially reused frequencies in its geographical area of coverage in a plurality of sectors, similar to the sectorization that is used in the base stations of conventional cellular radiotelephone networks. In FIG. 15, each ATC comprises three 120° sectors labeled 1, 2 and 3. The use of sectors in a radiotelephone base station, for example, is discussed in U.S. Pat. No. 6,311,074 entitled Base Station And Method For Covering A Cell Of A Cellular Mobile Radiotelephone System, and in U.S. Pat. No. 5,432,780 entitled High Capacity Sectorized Cellular Communication System, the disclosures of which are hereby incorporated herein in their entirety by reference. It will also be understood that fewer or more sectors also may be used, and/or that a number of sectors at each ATC within a network may be the same or different.

As shown in FIG. 15, according to some embodiments of the invention, staggered sectorization is used. Thus, over the plurality of four-cell reuse clusters of FIG. 15, frequency reuse of a particular frequency or set of frequencies, for example a frequency or set of frequencies F1, is staggered over different ATC sectors as it is reused over different four-cell clusters.

In particular, referring to FIG. 15, ATC 1520a reuses a particular frequency or set of frequencies in sector 2, as shown by arrow 1530a. ATC 1520b reuses the same frequency or frequencies in sector 3, as shown by arrow 1530b. ATC 1520c reuses this same frequency or frequencies in sector 1, as shown by arrow 1530c. Finally, ATC 1520d reuses the same frequency or frequencies in sector 3, as shown by arrow 1530d. Other staggered sectorizations of the same frequency are shown by other arrows in FIG. 15, but are not labeled for the sake of clarity.

When viewed globally from the perspective of a device, such as an airplane and/or other airborne vehicle, in any given direction, only one third of the total deployed reuses of a particular frequency or set of frequencies are radiating maximum or nearly maximum power in the given direction. Accordingly, the effective energy that is radiated by the ancillary terrestrial network at a given frequency in any given direction may be reduced. A given airborne device will therefore be exposed to only approximately one third the radiated power in the given frequency than may otherwise be the case if sectorization was maintained uniform across the ancillary terrestrial network.

It will be understood that in some embodiments of the invention, not all of the ATCs may need to stagger the reuse of a given satellite frequency or frequencies. In particular, in some embodiments, only some ATCs may stagger a reused frequency. Moreover, in other embodiments, staggering may be performed for some satellite radiotelephone frequencies but not for other satellite radiotelephone frequencies. Finally, as was already noted, staggered sectorization may be used in the base stations of conventional cellular radiotelephone systems, for example in a manner shown in FIG. 15.

According to embodiments of the present invention illustrated in FIGS. 13–15, a satellite radiotelephone system can include a space-based component(s), such as one or more satellites, configured to provide wireless radiotelephone communications over a satellite radiotelephone frequency band. The space-based component(s) can provide communications for a plurality of satellite radiotelephone cells (also referred to as coverage areas) such as illustrated, for example, in FIG. 13 or FIG. 14. More particularly, the satellite radiotelephone cells can be used to provide reuse of satellite radiotelephone frequencies so that the space-based component(s) reuses the same radiotelephone frequency or frequencies for radiotelephone communications in different geographic areas while reducing interference therebetween. As discussed above, FIG. 13 illustrates a seven cell reuse pattern of satellite radiotelephone frequencies in satellite radiotelephone cells, and FIG. 14 illustrates a nine cell reuse pattern of satellite radiotelephone frequencies in satellite radiotelephone cells.

A plurality of ancillary terrestrial components can be configured to provide an ancillary terrestrial network with each ancillary terrestrial component providing terrestrial radiotelephone communications for a respective terrestrial network cell. Moreover, the plurality of terrestrial components may be configured to terrestrially reuse at least one of the satellite radiotelephone frequencies within the satellite radiotelephone frequency band used by the space-based component, and the at least one of the satellite radiotelephone frequencies reused terrestrially may be reused in a staggered sectorization within the cells of the ancillary terrestrial network.

As discussed above, a satellite radiotelephone cell may have a diameter on the order of hundreds of kilometers, while an ancillary terrestrial network cell may have a diameter on the order of ten kilometers or less. A satellite radiotelephone cell, for example, may thus provide satellite radiotelephone communications over a relatively broad geographic area including a plurality of cities, while each city within the satellite radiotelephone cell may be serviced by a different terrestrial network with each terrestrial network including a respective plurality of ancillary terrestrial components such as base stations. Stated in other words, a plurality of separate ancillary terrestrial networks (with an example of a single ancillary terrestrial network being illustrated in FIG. 15) may provide terrestrial radiotelephone communications within a single satellite radiotelephone cell of a satellite communications network including a plurality of satellite radiotelephone cells such as illustrated, for example, in FIGS. 13 and 14.

More particularly, the satellite radiotelephone network may provide reuse of satellite radiotelephone frequencies within the satellite radiotelephone frequency band such that adjacent satellite radiotelephone cells do not use the same satellite radiotelephone frequencies. Moreover, components of an ancillary terrestrial network within a satellite radiotelephone cell may use satellite radiotelephone frequencies within the satellite radiotelephone frequency band other than frequencies used by the satellite radiotelephone cell for satellite communications within which the ancillary terrestrial network is located. Moreover, satellite radiotelephone frequencies used by the ancillary terrestrial network can be used by the space-based component to provide radiotelephone communications in other satellite radiotelephone cells not including the ancillary terrestrial network. Accordingly, interference between ancillary terrestrial networks and satellite radiotelephone cells using frequencies within the same satellite radiotelephone frequency band can be reduced and/or eliminated.

With a satellite communications network, such as illustrated in FIG. 13 or FIG. 14, one satellite radiotelephone frequency or a set of satellite radiotelephone frequencies can be reused in commonly numbered satellite radiotelephone cells. For example, a first set of satellite radiotelephone frequencies from the satellite radiotelephone frequency band can be reused by each of the satellite radiotelephone cells identified by reference number 1 in FIG. 13 to provide radio links for transmissions to/from a space-based component from/to radiotelephones in the satellite radiotelephone cells identified by reference number 1. A second set of satellite radiotelephone frequencies from the satellite radiotelephone frequency band can be reused by ancillary terrestrial components of an ancillary terrestrial network located within one of the satellite radiotelephone cells identified by the reference number 1 in FIG. 13.

The ancillary terrestrial network of FIG. 15, for example, can be located within one of the satellite radiotelephone cells identified by reference number 1 in FIG. 13. More particularly, the first and second sets of satellite radiotelephone frequencies can be mutually exclusive so that interference between transmissions to/from the space-based component in the satellite radiotelephone cell and transmissions to/from ancillary terrestrial components of the ancillary terrestrial network in the satellite radiotelephone cell can be reduced and/or eliminated. Moreover, satellite radiotelephone frequencies of the second set can be reused to provide transmissions to/from the space-based component in satellite radiotelephone cells other than the satellite radiotelephone cell(s) including an ancillary terrestrial network(s) using the second set of satellite radiotelephone frequencies.

An example of reuse of one or a set of the satellite radiotelephone frequencies of the second set used by the ancillary terrestrial network is illustrated with the arrows of FIG. 15. As shown, at least a portion of the ancillary terrestrial components can be divided into n directional sectors and one or more of the radiotelephone frequencies of the second set can be reused by the ancillary terrestrial network m times. Moreover, the ancillary terrestrial components can be grouped into reuse clusters or patterns indicated by the thick lines defining the reuse patterns 1510 discussed above. The arrows represent the reuse of one or a set of the radiotelephone frequencies no more than once in one directional sector of one ancillary terrestrial component in each reuse cluster. Moreover, the directions of the arrows are staggered to reduce an aggregate power of reused frequencies transmitted by the ancillary terrestrial network in any one direction.

As shown in FIG. 15, for example, a portion of the ancillary terrestrial components can be divided into 3 directional sectors (i.e. n=3), and one or a set of the radiotelephone frequencies can be reused 18 times as indicated by the 18 arrows (i.e. m=18). Moreover, the radiotelephone frequencies are shown as being reused 6 times in directional sectors pointing to X degrees, 6 times in directional sectors pointing to X+120 degrees, and 6 times in sectors pointing to X+240 degrees. In other words, an aggregate of radiated power transmitted by the ancillary terrestrial network at the reused frequency or frequencies in any direction in the example of FIG. 15 is no greater than approximately 1/n of a total radiated power transmitted by the ancillary terrestrial network at the reused frequency. As the directional sectors may not necessarily be aligned from ancillary terrestrial component to ancillary terrestrial component within an ancillary terrestrial network, an aggregate of radiated power transmitted in any direction may actually be less (or more) than 1/n of a total radiated power transmitted by the ancillary terrestrial network at the reused frequency or frequencies.

Additional reductions of aggregate radiated power in a particular direction may also be obtained by selectively rotating orientations of the ancillary terrestrial components such that directional sectors of ancillary terrestrial components are intentionally misaligned. In an ancillary terrestrial network including ancillary terrestrial components divided into three 120 degree sectors, for example, a first half of the ancillary terrestrial components may be aligned so that the directional sectors point to 90 degrees, 210 degrees, and 330 degrees, and a second half of the ancillary terrestrial components may be aligned so that the directional sectors point to 30 degrees, 150 degrees, and 270 degrees.

It also will be understood that techniques other than sectorization may be used to obtain randomization of the direction of frequency reuse and/or directional diversity in at least portions of the ancillary terrestrial network. For example, beam forming techniques may be used to randomize the direction of frequency reuse for beams that are reused in a given sector of the ancillary terrestrial network. Moreover, directions of frequency reuse may be randomized in ancillary terrestrial systems with terrestrial components divided into different numbers of sectors. For example, not every terrestrial component in terrestrial networks according to embodiments of the present invention must be divided into sectors, and those that are divided into sectors may be divided into different numbers of sectors.

According to embodiments of the present invention, providing communications can include reusing a radiotelephone frequency among a plurality of terrestrial components to provide radiotelephone communications for a plurality of mobile terminals. Moreover, reuse of the radiotelephone frequency can be randomized among the plurality of terrestrial components. In addition, the plurality of terrestrial components can be grouped into clusters of terrestrial components with at least one terrestrial component of each cluster transmitting to a plurality of directional sectors, and randomizing reuse of the radiotelephone frequency can include reusing the radiotelephone frequency in no more than one directional sector of a cluster of terrestrial components. Moreover, the clusters of terrestrial components may comprise clusters of adjacent terrestrial components.

Randomizing reuse of the radiotelephone frequency in no more than one directional sector of a cluster of terrestrial components can further include reusing the radiotelephone frequency so that a direction of the directional sectors reusing the radiotelephone frequency is staggered. As discussed above, the radiotelephone frequency can be used to provide downlinks from respective terrestrial components to receiving radiotelephones. In addition, the radiotelephone frequency reused among the plurality of terrestrial components can be within a band of satellite frequencies transmitted by a space-based component. Stated in other words, the radiotelephone frequency reused by the terrestrial components can also be used for satellite radiotelephone communications.

Similarly, a communications system can include means for reusing a radiotelephone frequency among a plurality of terrestrial components to provide radiotelephone communications for a plurality of mobile terminals, and means for randomizing reuse of the radiotelephone frequency among the plurality of terrestrial components. The plurality of terrestrial components can be grouped into clusters of terrestrial components with at least one terrestrial component of each cluster transmitting to a plurality of directional sectors, and the means for randomizing reuse of the radiotelephone frequency can include means for reusing the radiotelephone frequency in no more than one directional sector of a cluster of terrestrial components.

The means for randomizing reuse of the radiotelephone frequency in no more than one directional sector of a cluster of terrestrial components can also include means for reusing the radiotelephone frequency so that a direction of the directional sectors reusing the radiotelephone frequency is staggered. The radiotelephone frequency can also be used to provide down-links from respective terrestrial components to receiving radiotelephones.

In the drawings and specification, there have been disclosed typical preferred embodiments of the invention and, although specific terms are employed, they are used in a generic and descriptive sense only and not for purposes of limitation, the scope of the invention being set forth in the following claims.

What is claimed is:

1. A satellite radiotelephone system comprising:
   a space-based component that is configured to provide wireless radiotelephone communications over a satellite radiotelephone frequency band including a plurality of satellite radiotelephone frequencies; and
   a plurality of ancillary terrestrial components that are configured to terrestrially reuse at least one of the satellite radiotelephone frequencies, at least some of the ancillary terrestrial components terrestrially reusing the at least one of the satellite radiotelephone frequencies in a staggered sectorization;
   wherein at least some of the ancillary terrestrial components are divided into n directional sectors and the at least one of the satellite radiotelephone frequencies is reused within the at least some of the ancillary terrestrial components so that an aggregate radiated power transmitted by the at least some of the ancillary terrestrial components at the at least one of the satellite radiotelephone frequencies in any direction is no greater than approximately 1/n of a total radiated power transmitted by the at least some of the ancillary terrestrial components at the at least one of the satellite radiotelephone frequencies.

2. A satellite radiotelephone system according to claim 1 wherein the space-based component is configured to provide wireless radiotelephone communications for a coverage area including the plurality of ancillary terrestrial components using at least one satellite radiotelephone frequency other than the at least one of the satellite radiotelephone frequencies reused by the ancillary terrestrial components in the staggered sectorization.

3. A satellite radiotelephone system according to claim 2 wherein the space-based component is configured to provide a down-link to receiving radiotelephones in the coverage area using the at least one satellite radiotelephone frequency other than the at least one of the satellite radiotelephone frequencies reused by the ancillary terrestrial components in the staggered sectorization.

4. A satellite radiotelephone system according to claim 2 wherein the space-based component is configured to provide wireless radiotelephone communications for a second coverage area not including the plurality of ancillary terrestrial components reusing the at least one of the satellite radiotelephone frequencies, wherein the space-based component provides wireless radiotelephone communications for the second coverage area using the at least one of the satellite radiotelephone frequencies reused by the ancillary terrestrial components in the staggered sectorization.

5. A satellite radiotelephone system according to claim 1 wherein the at least one satellite radiotelephone frequency is used to provide radio downlinks from respective ancillary terrestrial components to receiving radiotelephones.

6. A satellite radiotelephone system comprising:
   a space-based component that is configured to provide wireless radiotelephone communications over a satellite radiotelephone frequency band including a plurality of satellite radiotelephone frequencies; and
   a plurality of ancillary terrestrial components that are configured to terrestrially reuse at least one of the satellite radiotelephone frequencies, at least some of the ancillary terrestrial components terrestrially reusing the at least one of the satellite radiotelephone frequencies in a staggered sectorization;
   wherein each of the ancillary terrestrial components is divided into n directional sectors and the at least one of the satellite radiotelephone frequencies is reused within the plurality of ancillary terrestrial components so that an aggregate radiated power transmitted by the plurality of ancillary terrestrial components at the at least one of the satellite radiotelephone frequencies in any direction is no greater than approximately 1/n of a total radiated power transmitted by the plurality of the ancillary terrestrial components at the at least one of the satellite-radiotelephone frequencies.

7. A satellite radiotelephone system according to claim 6 wherein n=3 so that each of the ancillary terrestrial components comprises three 120° sectors.

8. A satellite radiotelephone system according to claim 6 wherein the plurality of ancillary terrestrial components is divided into a plurality of reuse clusters, and with each reuse cluster reusing the at least one of the satellite radiotelephone frequencies no more than once.

9. A satellite radiotelephone system comprising:
   a space-based component that is configured to provide wireless radiotelephone communications over a satellite radiotelephone frequency band; and
   a plurality of ancillary terrestrial components grouped into clusters of ancillary terrestrial components at least one ancillary terrestrial component of each cluster transmitting to a plurality of directional sectors, wherein the clusters reuse a satellite radiotelephone frequency from the satellite radiotelephone frequency band in a single directional sector of a single ancillary terrestrial component of the respective cluster and wherein a direction of the directional sectors reusing the satellite radiotelephone frequency is staggered;
   wherein the ancillary terrestrial components transmitting to a plurality of directional sectors are divided into n directional sectors and the satellite radiotelephone frequency is reused within the clusters so that an aggregate of radiated power transmitted by the plurality of ancillary terrestrial components of the clusters at the satellite radiotelephone frequency in any direction is no greater than approximately 1/n of a total radiated power transmitted by the ancillary terrestrial components of the clusters at the satellite radiotelephone frequency.

10. A satellite radiotelephone system according to claim 9 wherein the space-based component is configured to provide wireless radiotelephone communications for a coverage area including the plurality of ancillary terrestrial components using a satellite radiotelephone frequency other than the satellite radiotelephone frequencies reused by the ancillary terrestrial components in the staggered directional sectors.

11. A satellite radiotelephone system according to claim 10 wherein the space-based component is configured to provide a down-link to receiving radiotelephones in the coverage area using a satellite radiotelephone frequency other than the satellite radiotelephone frequency reused by the ancillary terrestrial components in the staggered directional sectors.

12. A satellite radiotelephone system according to claim 10 wherein the space-based component is configured to provide wireless radiotelephone communications for a second coverage area not including the plurality of ancillary terrestrial components reusing the satellite radiotelephone frequency in the staggered directional sectors, wherein the space-based component provides wireless radiotelephone communications for the second coverage area using the satellite radiotelephone frequency reused by the ancillary terrestrial components in the staggered directional sectors.

13. A satellite radiotelephone system according to claim 9 wherein the satellite radiotelephone frequency is used to provide radio downlinks from respective ancillary terrestrial components to receiving radiotelephones.

14. A satellite radiotelephone system according to claim 9 wherein n=3 so that the ancillary terrestrial components transmitting to a plurality of directional sectors comprises three 120° sectors.

15. A satellite radiotelephone system according to claim 9 wherein each cluster reuses the satellite radiotelephone frequency no more than once.

16. A method of operating a satellite radiotelephone system comprising:
   providing wireless radiotelephone communications from a space-based component over a satellite radiotelephone frequency band including a plurality of satellite radiotelephone frequencies; and
   reusing at least one of the satellite radiotelephone frequencies to provide radiotelephone communications from a plurality of ancillary terrestrial components, wherein the at least one of the satellite radiotelephone frequencies is reused in a staggered sectorization;
   wherein at least some of the ancillary terrestrial components are divided into n directional sectors and the at least one of the satellite radiotelephone frequencies is reused within the at least some of the ancillary terrestrial components so that an aggregate of radiated power transmitted by the at least some of the ancillary terrestrial components at the at least one of the satellite radiotelephone frequencies in any direction is no greater than approximately 1/n of a total radiated power transmitted by the at least some of the ancillary terrestrial components at the at least one of the satellite radiotelephone frequencies.

17. A method according to claim 16 wherein providing wireless radiotelephone communications from the space-based component further comprises providing wireless radiotelephone communications for a coverage area including the plurality of ancillary terrestrial components using at least one satellite radiotelephone frequency other than the at least one of the satellite radiotelephone frequencies reused by the ancillary terrestrial components in the staggered sectorization.

18. A method according to claim 17 wherein providing wireless radiotelephone communications from the space-based component further comprises providing a down-link to receiving radiotelephones in the coverage area using the at least one satellite radiotelephone frequency other than the at least one of the satellite radiotelephone frequencies reused by the ancillary terrestrial components in the staggered sectorization.

19. A method according to claim 17 wherein providing wireless radiotelephone communications from the space-based component further comprises providing wireless radiotelephone communications for a second coverage area not including the plurality of ancillary terrestrial components reusing the at least one of the satellite radiotelephone frequencies, wherein wireless radiotelephone communications for the second coverage area are provided using the at least one of the satellite radiotelephone frequencies reused by the ancillary terrestrial components in the staggered sectorization.

20. A method according to claim 16 wherein the at least one satellite radiotelephone frequency is used to provide radio downlinks from respective ancillary terrestrial components to receiving radiotelephones.

21. A method of operating a satellite radiotelephone system comprising:
providing wireless radiotelephone communications from a space-based component over a satellite radiotelephone frequency band including a plurality of satellite radiotelephone frequencies; and
reusing at least one of the satellite radiotelephone frequencies to provide radiotelephone communications from a plurality of ancillary terrestrial components, wherein the at least one of the satellite radiotelephone frequencies is reused in a staggered sectorization;
wherein each of the ancillary terrestrial components is divided into n directional sectors and the at least one of the satellite radiotelephone frequencies is reused within the plurality of ancillary terrestrial components so that an aggregate of radiated power transmitted by the plurality of ancillary terrestrial components at the at least one of the satellite radiotelephone frequencies in any direction is no greater than approximately 1/n of a total radiated power transmitted by the plurality of the ancillary terrestrial components at the at least one of the satellite radiotelephone frequencies.

22. A method according to claim 21 wherein n=3 so that each of the ancillary terrestrial components comprises three 120° sectors.

23. A method according to claim 21 wherein the plurality of ancillary terrestrial components is divided into a plurality of reuse clusters with each reuse cluster reusing the at least one of the satellite radiotelephone frequencies no more than once.

24. A method of operating a satellite radiotelephone system comprising:
providing wireless radiotelephone communications from a space-based component over a satellite radiotelephone frequency band; and
reusing a satellite radiotelephone frequency from the satellite radiotelephone frequency band to provide radiotelephone communications from a plurality of ancillary terrestrial components wherein the plurality of ancillary terrestrial components are grouped into clusters of terrestrial components with at least one ancillary terrestrial component of each cluster transmitting to a plurality of directional sectors and wherein a direction of the directional sectors reusing the satellite radiotelephone frequency is staggered;
wherein each of the ancillary terrestrial components transmitting to a plurality of directional sectors is divided into n directional sectors and the satellite radiotelephone frequency is reused within the clusters of ancillary terrestrial components so that an aggregate of radiated power transmitted by the clusters of ancillary terrestrial components at the satellite radiotelephone frequency in any direction is no greater than approximately 1/n of a total radiated power transmitted by the clusters of the ancillary terrestrial components at the satellite radiotelephone frequency.

25. A method according to claim 24 wherein providing wireless radiotelephone communications from the space-based component further comprises providing wireless radiotelephone communications for a coverage area including the plurality of ancillary terrestrial components using a satellite radiotelephone frequency other than the satellite radiotelephone frequency reused by the ancillary terrestrial components in the staggered directional sectors.

26. A method according to claim 25 wherein providing wireless radiotelephone communications from the space-based component further comprises providing a down-link to receiving radiotelephones in the coverage area using the satellite radiotelephone frequency other than the satellite radiotelephone frequency reused by the clusters of ancillary terrestrial components in the staggered directional sectors.

27. A method according to claim 25 wherein providing wireless radiotelephone communications from the space-based component further comprises providing wireless radiotelephone communications for a second coverage area not including the plurality of ancillary terrestrial components reusing the satellite radiotelephone frequency in the staggered directional sectors, wherein wireless radiotelephone communications are provided for the second coverage area by the space-based component using the satellite radiotelephone frequency reused by the ancillary terrestrial components in the staggered directional sectors.

28. A method according to claim 24 wherein the satellite radiotelephone frequency is used to provide radio downlinks from respective ancillary terrestrial components to receiving radiotelephones.

29. A method according to claim 24 wherein n=3 so that the ancillary terrestrial components transmitting to a plurality of directional sectors comprises three 120° sectors.

30. A method according to claim 24 wherein each cluster reuses the satellite radiotelephone frequency no more than once.

31. A radiotelephone system comprising:
a plurality of terrestrial components grouped into clusters of terrestrial components wherein at least one terrestrial component of each cluster transmits to a plurality of directional sectors, wherein a plurality of the clusters reuse a radiotelephone frequency in a single directional sector of a single terrestrial component of the respective cluster and wherein a direction of the directional sectors reusing the radiotelephone frequency is staggered;
wherein each of the terrestrial components transmitting to a plurality of directional sectors is divided into n directional sectors and the radiotelephone frequency is reused within the clusters of terrestrial components so that an aggregate of radiated power transmitted by the clusters of terrestrial components at the radiotelephone frequency in any direction is no greater than approximately 1/n of a total radiated power transmitted by the clusters of terrestrial components at the radiotelephone frequency.

32. A radiotelephone system according to claim 31 wherein the radiotelephone frequency is used to provide radio downlinks from respective terrestrial components to receiving radiotelephones.

33. A radiotelephone system according to claim 31 wherein n=3 so that each of the ancillary terrestrial components transmitting to a plurality of directional sectors comprises three 120° sectors.

34. A radiotelephone system according to claim 31 wherein each cluster reuses the radiotelephone frequency no more than once.

35. A radiotelephone system according to claim 31 wherein the radiotelephone frequency reused by the plurality of clusters is within a band of satellite frequencies transmitted by a space-based component.

36. A method of operating a radiotelephone system comprising:
   reusing a radiotelephone frequency to provide radiotelephone communications from a plurality of terrestrial components wherein the plurality of terrestrial components are grouped into clusters of terrestrial components with at least one terrestrial component of each cluster transmitting to a plurality of directional sectors and wherein a direction of the directional sectors reusing the radiotelephone frequency is staggered;
   wherein the terrestrial components transmitting to a plurality of directional sectors are divided into n directional sectors and the radiotelephone frequency is reused within the clusters of terrestrial components so that an aggregate of radiated power transmitted by the clusters of terrestrial components at the radiotelephone frequency in any direction is no greater than approximately 1/n of a total radiated power transmitted by the plurality of the terrestrial components at the radiotelephone frequency.

37. A method according to claim 36 wherein the radiotelephone frequency is used to provide radio downlinks from respective terrestrial components to receiving radiotelephones.

38. A method according to claim 36 wherein n=3 so that the terrestrial components transmitting to a plurality of directional sectors comprises three 120° sectors.

39. A method according to claim 36 wherein each cluster reuses the radiotelephone frequency no more than once.

40. A method according to claim 36 wherein the radiotelephone frequency reused by the plurality of clusters is within a band of satellite frequencies transmitted by a space-based component.

41. A method of providing communications comprising:
   reusing a radiotelephone frequency among a plurality of terrestrial components to provide radiotelephone communications for a plurality of mobile terminals; and
   randomizing reuse of the radiotelephone frequency among the plurality of terrestrial components;
   wherein the plurality of terrestrial components are grouped into clusters of terrestrial components with at least one terrestrial component of each cluster transmitting to a plurality of directional sectors wherein randomizing reuse of the radiotelephone frequency comprises reusing the radiotelephone frequency in no more than one directional sector of a cluster of terrestrial components;
   wherein the terrestrial components transmitting to a plurality of directional sectors are divided into n directional sectors and the radiotelephone frequency is reused within the clusters of terrestrial components so that an aggregate of radiated power transmitted by the clusters of terrestrial components at the radiotelephone frequency in any direction is no greater than approximately 1/n of a total radiated power transmitted by the plurality of the terrestrial components at the radiotelephone frequency.

42. A method according to claim 41 wherein randomizing reuse of the radiotelephone frequency in no more than one directional sector of a cluster of terrestrial components comprises reusing the radiotelephone frequency so that a direction of the directional sectors reusing the radiotelephone frequency is staggered.

43. A method according to claim 41 wherein the radiotelephone frequency is used to provide downlinks from respective terrestrial components to receiving radiotelephones.

44. A method according to claim 41 wherein the radiotelephone frequency reused among the plurality of terrestrial components is within a band of satellite frequencies transmitted by a space-based component.

45. A communications system comprising:
   means for reusing a radiotelephone frequency among a plurality of terrestrial components to provide radiotelephone communications for a plurality of mobile terminals; and
   means for randomizing reuse of the radiotelephone frequency among the plurality of terrestrial components;
   wherein the plurality of terrestrial components are grouped into clusters of terrestrial components with at least one terrestrial component of each cluster transmitting to a plurality of directional sectors wherein the means for randomizing reuse of the radiotelephone frequency comprises means for reusing the radiotelephone frequency in no more than one directional sector of a cluster of terrestrial components;
   wherein the terrestrial components transmitting to a plurality of directional sectors are divided into n directional sectors and the radiotelephone frequency is reused within the clusters of terrestrial components so that an aggregate of radiated power transmitted by the clusters of terrestrial components at the radiotelephone frequency in any direction is no greater than approximately 1/n of a total radiated power transmitted by the plurality of the terrestrial components at the radiotelephone frequency.

46. A communications system according to claim 45 wherein the means for randomizing reuse of the radiotelephone frequency in no more than one directional sector of a cluster of terrestrial components comprises means for reusing the radiotelephone frequency so that a direction of the directional sectors reusing the radiotelephone frequency is staggered.

47. A communications system according to claim 45 wherein the radiotelephone frequency is used to provide downlinks from respective terrestrial components to receiving radiotelephones.

48. A communications system according to claim 45 wherein the radiotelephone frequency reused among the plurality of terrestrial components is within a band of satellite frequencies transmitted by a space-based component.

\* \* \* \* \*